US012798973B2

(12) United States Patent
Sugiura et al.

(10) Patent No.: US 12,798,973 B2
(45) Date of Patent: Nov. 17, 2026

(54) CRYSTAL, POWDER, BLOCK MATERIAL, POROUS OBJECT, BONE SUBSTITUTE MATERIAL, AND ORAL BONE SUBSTITUTE MATERIAL OF CALCIUM PHOSPHATE, METHOD FOR PRODUCING CALCIUM PHOSPHATE CRYSTAL, METHOD FOR PRODUCING BLOCK MATERIAL, AND METHOD FOR PRODUCING POROUS OBJECT

(71) Applicant: NATIONAL INSTITUTE OF ADVANCED INDUSTRIAL SCIENCE AND TECHNOLOGY, Tokyo (JP)

(72) Inventors: Yuki Sugiura, Takamatsu (JP); Yoji Makita, Takamatsu (JP)

(73) Assignee: NATIONAL INSTITUTE OF ADVANCED INDUSTRIAL SCIENCE AND TECHNOLOGY (JP)

( * ) Notice: Subject to any disclaimer, the term of this patent is extended or adjusted under 35 U.S.C. 154(b) by 1143 days.

(21) Appl. No.: 17/796,995

(22) PCT Filed: Feb. 4, 2021

(86) PCT No.: PCT/JP2021/004149
§ 371 (c)(1),
(2) Date: Aug. 2, 2022

(87) PCT Pub. No.: WO2021/157662
PCT Pub. Date: Aug. 12, 2021

(65) Prior Publication Data

US 2023/0056160 A1 Feb. 23, 2023

(30) Foreign Application Priority Data

Feb. 4, 2020 (JP) ................................ 2020-017459

(51) Int. Cl.
*C01B 25/45* (2006.01)
*A61K 6/838* (2020.01)
(Continued)

(52) U.S. Cl.
CPC .............. *C01B 25/45* (2013.01); *A61K 6/838* (2020.01); *A61L 27/12* (2013.01); *A61L 27/54* (2013.01);
(Continued)

(58) Field of Classification Search
None
See application file for complete search history.

(56) References Cited

U.S. PATENT DOCUMENTS

2001/0024662 A1* 9/2001 Yang ...................... A61L 27/10 424/618
2010/0249925 A1* 9/2010 Blunn ..................... C25D 9/04 427/2.24
(Continued)

FOREIGN PATENT DOCUMENTS

CN 103159197 A 6/2013
JP H 08245208 A 9/1996
(Continued)

OTHER PUBLICATIONS

International Search Report mailed Apr. 13, 2021 in corresponding PCT International Application No. PCT/JP2021/004149.
(Continued)

*Primary Examiner* — John J Figueroa
(74) *Attorney, Agent, or Firm* — OSTROLENK FABER LLP

(57) ABSTRACT

A crystal of a calcium phosphate that is any one selected from the group consisting of octacalcium phosphate, hydroxyapatite, fluorapatite, chlorapatite and carbonate apatite, in which a part of a plurality of calcium ions in a crystal
(Continued)

structure of the crystal are replaced with a silver ion or a copper ion.

19 Claims, 11 Drawing Sheets

(51) Int. Cl.

| | |
|---|---|
| ***A61L 27/12*** | (2006.01) |
| ***A61L 27/54*** | (2006.01) |
| ***C04B 35/447*** | (2006.01) |
| ***C04B 38/00*** | (2006.01) |
| ***C04B 41/85*** | (2006.01) |

(52) U.S. Cl.
CPC ........ *C04B 35/447* (2013.01); *C04B 38/0022* (2013.01); *C04B 41/85* (2013.01)

(56) References Cited

U.S. PATENT DOCUMENTS

| | | | | |
|---|---|---|---|---|
| 2010/0286790 | A1* | 11/2010 | Gruner | A61L 27/54<br>427/2.24 |
| 2017/0119932 | A1* | 5/2017 | Mawatari | A61L 27/54 |
| 2017/0173213 | A1* | 6/2017 | Yates | C25D 9/04 |
| 2019/0177229 | A1* | 6/2019 | Ikoma | A61L 27/425 |
| 2022/0356070 | A1* | 11/2022 | Ishikawa | C01B 25/32 |

FOREIGN PATENT DOCUMENTS

| | | | |
|---|---|---|---|
| JP | 2018016523 | A | 2/2018 |
| JP | 2019077720 | A | 5/2019 |
| WO | WO 2016046517 | A1 | 3/2016 |

OTHER PUBLICATIONS

Y. Sugiura, et al., "Fabrication of octacalcium phosphate block through a dissolution preparation reaction using a calcium sulphate hemihydrate block as a precursor", Journal of Materials Science: Materials in Medicine, Sep. 2018, 29:151, pp. 1-8.

Y. Sugiura & Y. Makita, "Sodium induces octacalcium phosphate formation and enhances its layer structure by affecting the hydrous layer phosphate", Crystal Growth & Design, Aug. 2018, 18:6165, pp. 6165-6171.

T. Akiyama et al., "Silver oxide-containing hydroxyapatite coating has in vivo antibacterial activity in the rat tibia", Journal of Orthopaedic Research, Apr. 2013, 31:1195, pp. 1195-1200.

* cited by examiner

| Ag CONCENTRATION (mmol/L) | BEFORE SHAKING IN PBS | | AFTER SHAKING IN PBS | |
|---|---|---|---|---|
| | RGB | HSB | RGB | HSB |
| 0 | 246, 245, 243 | 40, 1, 96 | 246, 246, 243 | 60, 1, 96 |
| 5 | 248, 248, 244 | 60, 1, 97 | 238, 239, 237 | 90, 0, 93 |
| 10 | 247, 247, 244 | 60, 1, 96 | 234, 233, 232 | 30, 0, 91 |
| 20 | 248, 247, 243 | 48, 2, 97 | 233, 234, 234 | 180, 0, 91 |
| 50 | 228, 227, 221 | 51, 3, 89 | 224, 223, 224 | 300, 0, 87 |
| 100 | 196, 183, 131 | 48, 33, 76 | 204, 194, 201 | 318, 3, 80 |
| 250 | 195, 171, 96 | 45, 50, 76 | 195, 177, 189 | 320, 9, 76 |
| 500 | 195, 173, 96 | 46, 50, 76 | 190, 176, 187 | 312, 7, 74 |

CRYSTAL, POWDER, BLOCK MATERIAL, POROUS OBJECT, BONE SUBSTITUTE MATERIAL, AND ORAL BONE SUBSTITUTE MATERIAL OF CALCIUM PHOSPHATE, METHOD FOR PRODUCING CALCIUM PHOSPHATE CRYSTAL, METHOD FOR PRODUCING BLOCK MATERIAL, AND METHOD FOR PRODUCING POROUS OBJECT

REFERENCES TO RELATED APPLICATIONS

The present application is a 35 U.S.C. § 371 national stage application of PCT/JP2021/004149, filed Feb. 4, 2021, which claims priority to Japanese Patent Application No. 2020-017459, filed Feb. 4, 2020, the contents of which are incorporated herein by reference.

TECHNICAL FIELD

The present invention relates to a medical material and a producing method thereof. In more detail, the present invention relates to a crystal, a powder, a block material, a porous material, a bone substitute material, and an oral bone substitute material of a calcium phosphate that can be used for the tissue regeneration of bones, teeth and the like in medical fields or medical related fields and have an antibacterial property, a method for producing a calcium phosphate crystal, a method for producing a block material, and a method for producing a porous material.

BACKGROUND ART

Materials made of a calcium phosphate are in use as materials for artificial bone substitute materials that are used in oral surgery, orthopedic surgery and the like.

Examples of the materials made of a calcium phosphate include dicalcium hydrogen phosphate anhydrate (DCPA, $CaHPO_4$), calcium hydrogen phosphate dihydrate (DCPD, $CaHPO_4 \cdot 2H_2O$), octacalcium phosphate (OCP, $Ca_8(HPO_4)_2(PO_4)_4 \cdot 5H_2O$), α-tricalcium phosphate (α-TCP, $Ca_3(PO_4)_2$), β-tricalcium phosphate (β-TCP, $Ca_3(PO_4)_2$), hydroxyapatite (HAp, $Ca_{10}(PO_4)_6(OH)_2$), tetracalcium phosphate (TTCP, $Ca_4(PO_4)_2O$) and the like.

These calcium phosphates have different properties (easiness in forming, a bone replacement property and the like) and are appropriately selected and used depending on uses.

HAp is a calcium phosphate that is being most widely used. HAp has the lowest solubility at a near-neutral pH and is least likely to dissolve in living bodies.

As materials that are analogous to HAp, there are fluorapatite (FAp, $Ca_{10}(PO_4)_6F_2$) in which two hydroxyl groups in the chemical composition formula of HAp are replaced with fluorine atoms and chlorapatite (ClAp, $Ca_{10}(PO_4)_6Cl_2$) in which the hydroxyl groups are replaced with chlorine atoms.

In addition, carbonate apatite ($CO_3$Ap, $Ca_{10-a}(PO_4)_{6-b}(CO_3)_c(OH)_{2-d}$) in which some of a phosphate group and the like (a phosphate group, a hydroxyl group, oxygen, fluorine and chlorine) of HAp are replaced with a carbonate group is also such a material. It is known that, when the content of carbonic acid in carbonate apatite increases, the solubility increases.

HAp and $CO_3$Ap have a stable crystal structure compared with OCP to be described below. Therefore, it was not easy to directly replace some of calcium ions contained with other cations. Therefore, it was difficult to impart a new function such as an antibacterial property to HAp, $CO_3$Ap and the like by, for example, inserting other cations into the crystal structure for replacement.

On the other hand, OCP is a candidate material for excellent bone replacement-type bone substitute materials having a more favorable bone replacement property (a property of a material being inserted into a bone for replacement) and biocompatibility than HAp, α-TCP and β-TCP. However, OCP has a problem in that molding of an OCP powder by sintering is difficult.

In addition, even for OCP, there has been no established method for efficiently replacing some of calcium ions in the crystal structure with other cations, in particular, cations that form a base having a slow solubility.

As a more detailed description of OCP, Non Patent Literature 1 discloses a method for preparing an OCP block from a precursor block made of calcium sulfate hemihydrate (CSH) not by sintering but by a dissociation precipitation reaction.

In addition, Non Patent Literature 2 discloses experiment results suggesting that, at the time of forming OCP from calcium hydrogen phosphate dihydrate (DCPD), when a sodium ion is appropriately incorporated, OCP formation is promoted, and, when a sodium ion is excessively incorporated, the stability of OCP deteriorates.

In the orthopedic surgery and oral surgery regions where bone substitute materials are mainly used, surgical field infection, that is, postoperative infection is known as a serious complication. Since bone substitute materials themselves are helpless against infection, once bone substitute materials are infected, there is no other way but to remove the corresponding portion, and the prognosis becomes bad. The disorder occurs with a probability of several percentages in all operative procedures.

From the viewpoint of suppressing the occurrence of postoperative infectious diseases, bone substitute materials desirably exhibit an antibacterial property for a long period of time. For example, for titanium artificial joints having a surface coated with HAp, a technique for imparting an antibacterial property to a bone substitute material by incorporating an antibacterial substance into the HAp coating is known (Non Patent Literature 3).

However, there has been no example of an antibacterial property being imparted to bone substitute materials, in particular, bone replacement-type bone substitute materials, and, furthermore, in some cases, postoperative infection occurs several years after operations, and thus an antibacterial property is required to be persistently imparted.

In the oral surgery field, a change in the color of bone substitute materials after operations is not desirable from the aesthetic viewpoint.

An example of the antibacterial substance that is used to impart an antibacterial property to bone substitute materials is silver. In a case where a silver salt is precipitated on and attached to the surface of a bone substitute material, there is a problem in that the surface is gradually tinged with black color, and the aesthetic property is impaired.

CITATION LIST

Non Patent Literature

[Non Patent Literature 1]

Y. Sugiura et al. "Fabrication of octacalcium phosphate block through a dissolution-preparation reaction using a calcium sulphate hemihydrate block as a precursor" Journal of Materials Science: Materials in Medicine 2018, 29: 151

[Non Patent Literature 2]

Y. Sugiura and Y. Makita "Sodium induces octacalcium phosphate formation and enhances its layer structure by affecting the hydrous layer phosphate" Crystal Growth & Design 2018, 18: 6165

[Non Patent Literature 3]

Akiyama T et al. "Silver oxide-containing hydroxyapatite coating has in vivo antibacterial activity in the rate tibia" Journal of Orthopaedic Research 2013, 31: 1195

SUMMARY OF INVENTION

Technical Problem

The present invention has been made in consideration of the above-described circumstances, and an objective of the present invention is to provide a crystal, a powder, a block material, a porous material, a bone substitute material, and an oral bone substitute material of a calcium phosphate exhibiting an antibacterial property by inserting a silver ion and/or a copper ion that is to be supported in the crystal structure of the calcium phosphate, a method for producing a calcium phosphate crystal, a method for producing a block material, and a method for producing a porous material.

Solution to Problem

The present inventors repeated intensive studies regarding means for solving the above-described problems and found that the above-described problems are solved by aspects to be described below.

(1) A crystal of a calcium phosphate according to a first aspect is a crystal of a calcium phosphate that is any one selected from the group consisting of octacalcium phosphate, hydroxyapatite, fluorapatite, chlorapatite and carbonate apatite, in which a part of a plurality of calcium ions in a crystal structure of the crystal are replaced with a silver ion or a copper ion.

(2) In the crystal of a calcium phosphate according to the first aspect, the calcium phosphate may be octacalcium phosphate.

(3) In the crystal of a calcium phosphate according to the first aspect, the calcium phosphate may be hydroxy-apatite.

(4) In the crystal of a calcium phosphate according to the first aspect, the calcium phosphate may be carbonate apatite.

(5) In the crystal of a calcium phosphate according to any one of the (1) to (4), a content rate of a silver atom or a copper atom may be 0.01 atom % or more and 13.00 atom % or less.

(6) In the crystal of a calcium phosphate according to any one of the (1) to (4), a content rate of a silver atom or a copper atom may be 0.10 atom % or more and 10.00 atom % or less.

(7) In the crystal of a calcium phosphate according to any one of the (1) to (4), a content rate of a silver atom or a copper atom may be 1.00 atom % or more and 7.00 atom % or less.

(8) In the crystal of a calcium phosphate according to any one of the (1) to (4), a content rate of a silver atom or a copper atom may be 2.00 atom % or more and 5.00 atom % or less.

(9) A powder according to a second aspect containing the crystal of a calcium phosphate according to any one of the (1) to (8).

(10) A block material according to a third aspect containing the crystal of a calcium phosphate according to any one of the (1) to (8).

(11) A porous material according to a fourth aspect containing the crystal of a calcium phosphate according to any one of the (1) to (8).

(12) A bone substitute material according to a fifth aspect containing the crystal of a calcium phosphate according to any one of the (1) to (8).

(13) An oral bone substitute material according to a sixth aspect containing the crystal of a calcium phosphate according to any one of the (1) to (8).

(14) A method for producing a crystal of a calcium phosphate according to a seventh aspect is a method for producing a crystal of a calcium phosphate that is any one selected from the group consisting of octacalcium phosphate, hydroxyapatite, fluorapatite, chlorapatite and carbonate apatite, including a process of dissolving a silver-containing composition or a copper-containing composition in a solvent containing water to prepare a solution containing a complex ion of a silver ion or a copper ion and a process of adding a compound containing phosphoric acid, hydrogen and calcium to the solution to form a crystal of octacalcium phosphate, in which a part of a plurality of calcium ions in a structure of the crystal of the calcium phosphate are replaced with a silver ion or a copper ion.

(15) In the method for producing a crystal of a calcium phosphate according to the (14), the calcium phosphate may be octacalcium phosphate.

(16) In the method for producing a crystal of a calcium phosphate according to the (14), the calcium phosphate may be hydroxyapatite, and the producing method may further include a process of converting a phase/phases of the crystal of the octacalcium phosphate into a crystal of hydroxyapatite while maintaining a solid state by hydrolysis or a hydrothermal reaction in a phase conversion solution.

(17) In the method for producing a crystal of a calcium phosphate according to the (14), the calcium phosphate may be carbonate apatite, and the producing method may further include a process of converting a phase/phases of the crystal of the octacalcium phosphate into a crystal of carbonate apatite while maintaining a solid state by a carbonation treatment in a phase conversion solution.

(18) In the method for producing a crystal of a calcium phosphate according to any one of (14) to (17), a concentration of the silver ion or the copper ion in the solution in the process of preparing the solution may be in a range of 0.1 mmol/L to 200 mmol/L.

(19) In the method for producing a crystal of a calcium phosphate according to any one of (14) to (17), a concentration of the silver ion or the copper ion in the solution in the process of preparing the solution may be in a range of 2.5 mmol/L to 30 mmol/L.

(20) A method for producing a block material according to an eighth aspect is a method for producing a block material containing a crystal of a calcium phosphate that is any one selected from the group consisting of octacalcium phosphate, hydroxyapatite, fluorapatite, chlorapatite and carbonate apatite, including a process of immersing a solid composition made of ceramic containing at least one of calcium and phosphoric acid in a solution containing the other of calcium and phosphoric acid and a silver ion, a complex ion of silver, a copper ion or a complex ion of copper and converting some of the solid composition to a crystal of octacalcium phosphate to obtain the block material, in which a part of a plurality of calcium ions in a structure of the crystal of the octacalcium phosphate are replaced with a silver ion or a copper ion.

(21) In the method for producing a block material according to the (20), the calcium phosphate may be octacalcium phosphate.

(22) In the method for producing a block material according to the (20), the calcium phosphate may be hydroxyapatite, and the producing method may further include a process of immersing the block material in a phase conversion solution and converting a phase/phases of the crystal of the octacalcium phosphate into a crystal of hydroxyapatite while maintaining a solid state by hydrolysis or a hydrothermal reaction in the phase conversion solution.

(23) In the method for producing a block material according to the (20), the calcium phosphate may be carbonate apatite, and the producing method may further include a process of immersing the block material in a phase conversion solution and converting a phase/phases of the crystal of the octacalcium phosphate into a crystal of carbonate apatite while maintaining a solid state by a carbonation treatment in the phase conversion solution.

(24) In the method for producing a block material according to any one of the (20) to (23), a concentration of the silver ion or the copper ion in the solution may be in a range of 0.1 mmol/L to 200 mmol/L.

(25) In the method for producing a block material according to any one of the (20) to (23), a concentration of the silver ion or the copper ion in the solution may be in a range of 0.1 mmol/L to 200 mmol/L.

(26) A method for producing a porous material according to a ninth aspect is a method for producing a porous material containing a crystal of a calcium phosphate that is any one selected from the group consisting of octacalcium phosphate, hydroxyapatite, fluorapatite, chlorapatite and carbonate apatite, including a process of immersing a solid composition made of ceramic containing at least one of calcium and phosphoric acid in a solution containing the other of calcium and phosphoric acid and a silver ion, a complex ion of silver, a copper ion or a complex ion of copper and converting some of the solid composition to a crystal of octacalcium phosphate to obtain the porous material, in which a part of a plurality of calcium ions in a structure of the crystal of the octacalcium phosphate are replaced with a silver ion or a copper ion.

(27) In the method for producing a porous material according to the (26), the calcium phosphate may be octacalcium phosphate.

(28) In the method for producing a porous material according to the (26), the calcium phosphate may be hydroxyapatite, and the producing method may further include a process of immersing the porous material in a phase conversion solution and converting a phase/phases of the crystal of the octacalcium phosphate into a crystal of hydroxyapatite while maintaining a solid state by hydrolysis or a hydrothermal reaction in the phase conversion solution.

(29) In the method for producing a porous material according to the (26), the calcium phosphate may be carbonate apatite, and the producing method may further include a process of immersing the block material in a phase conversion solution and converting a phase/phases of the crystal of the octacalcium phosphate into a crystal of carbonate apatite while maintaining a solid state by a carbonation treatment in the phase conversion solution.

(30) In the method for producing a porous material according to any one of the (26) to (29), a concentration of the silver ion or the copper ion in the solution may be in a range of 0.1 mmol/L to 200 mmol/L.

(31) In the method for producing a porous material according to any one of the (26) to (29), a concentration of the silver ion or the copper ion in the solution may be in a range of 2.5 mmol/L to 30 mmol/L.

Effects of the Invention

According to the crystal, the powder, the block material, the porous material, the bone substitute material, and the oral bone substitute material of the calcium phosphate according to the aspects of the present invention, it is possible to impart an antibacterial property to bone substitute materials.

In addition, according to the method for producing a crystal, a powder, a block material, a porous material, a bone substitute material, and an oral bone substitute material of a calcium phosphate according to the aspects of the present invention, it is possible to produce bone substitute materials having an antibacterial property.

In a case where the calcium phosphate is OCP, it is possible to hold an antibacterial property that is imparted to bone substitute materials for a long period of time.

DESCRIPTION OF EMBODIMENTS

Hereinafter, embodiments for carrying out the present invention will be described in detail with appropriate reference to the drawings.

First Embodiment

"Crystal of Replacement-Type Calcium Phosphate"

A first embodiment of the present invention is a crystal of a calcium phosphate.

The calcium phosphate in the crystal of a calcium phosphate of the present embodiment is a crystal of any one selected from the group consisting of OCP, HAp, FAp, ClAp and $CO_3Ap$, and a part of a plurality of calcium ions in the crystal structure of the crystal are replaced with silver ions or copper ions.

Some of the plurality of calcium ions may be replaced with a silver ion and a copper ion.

The crystal of the replacement-type calcium phosphate of the present embodiment is a crystal of replacement-type OCP that is produced by a method different from the conventional coprecipitation method or hydrolysis method or replacement-type HAp, FAp, ClAp or $CO_3Ap$ that is produced by a method in which the above-described crystal of replacement-type OCP is used as a starting material.

In the method for producing the above-described crystal of replacement-type OCP, a poorly-soluble metal salt containing a silver ion or a copper ion is dispersed/solubilized by forming a complex ion in the presence of an ammonium ion or the like. In addition, the obtained liquid and a solid containing phosphoric acid and calcium such as DCPD are reacted with each other, thereby producing a crystal of replacement-type OCP. In the crystal of replacement-type OCP that is produced by the present method, a calcium ion is replaced with a silver ion or a copper ion on a high level that is not possible to achieve by the conventional coprecipitation method or hydrolysis method.

In addition, when HAp, FAp, ClAp or $CO_3Ap$ is produced using the crystal of replacement-type OCP that is obtained as described above as a starting material, it is possible to replace a calcium ion with a silver ion or a copper ion on a high level that was not possible by the conventional methods even in the production of these Ap's.

The content rate of a silver atom or a copper atom in the crystal of the calcium phosphate may be 0.01 atom % or more and 13.00 atom % or less. The content rate may be set to 0.10 atom % or more and 10.00 atom % or less, may be set to 1.00 atom % or more and 7.00 atom % or less and may be set to 2.00 atom % or more and 5.00 atom % or less.

In addition, the lower limit value of concentrations of the silver atom or the copper atom may be 0.25, 0.50, 0.75, 1.25, 1.50 or 1.75 atom %.

Figure 1:
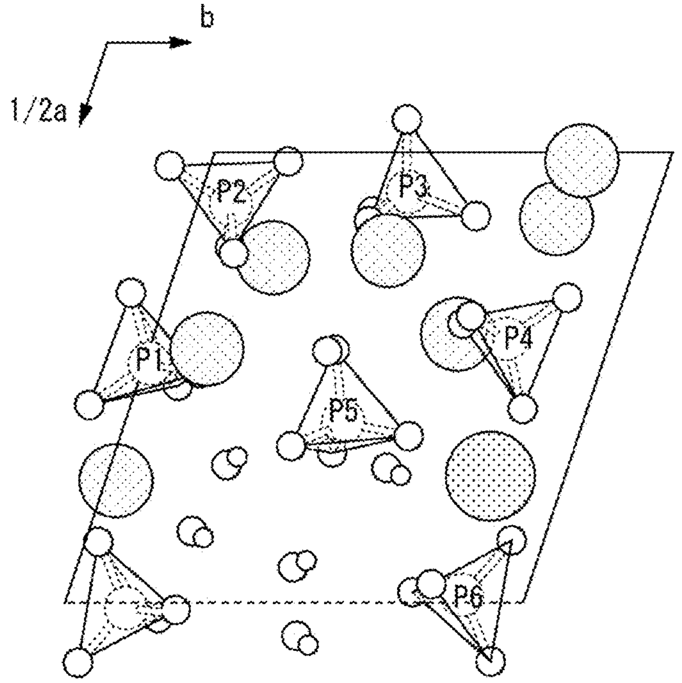
FIG. 1 is a schematic view of an example of the structure of a crystal of OCP according to a first embodiment of the present invention.
Figure 2:
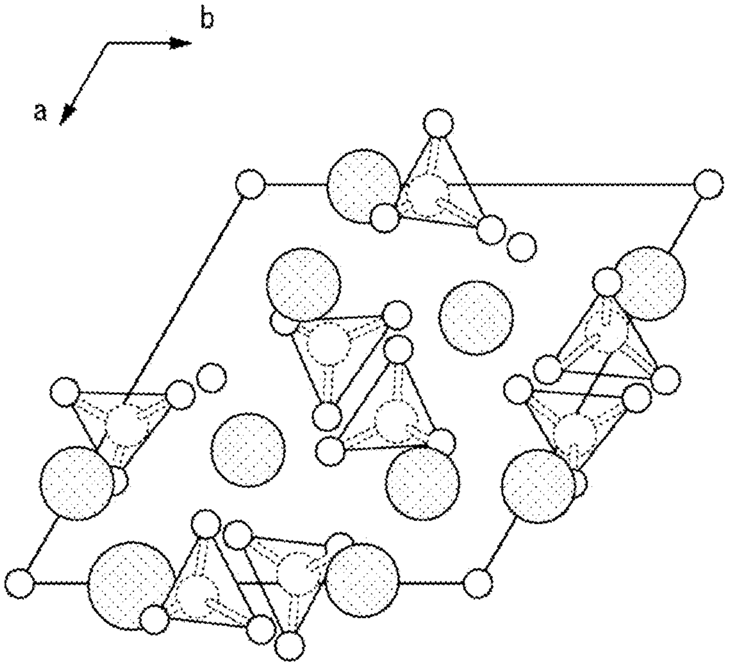
FIG. 2 is a schematic view of an example of the structure of a crystal of HAp according to the first embodiment of the present invention.

FIG. 1 and FIG. 2 are schematic views of examples of the structures of the crystals of calcium phosphates (the case of OCP and the case of HAp) according to the first embodiment of the present invention.

"The crystal of a calcium phosphate" in the description of the present specification means a crystal holding the crystal structure of OCR HAp, FAp, ClAp or $CO_3Ap$, in which a part of a plurality of calcium ions in the crystal structure are replaced with different kinds of ions such as silver ions and copper ions. Crystals in which an ion or composition other than the silver ion or the copper ion that is inserted for replacement is further incorporated into the crystal structure are also included in the definition of "the crystal of a calcium phosphate". For example, in the crystal of a calcium phosphate, in addition to the different kind of ion that is inserted for replacement, a composition having a functional group that chemically bonds to calcium may be incorporated.

In addition, in a case where ions, atoms, molecules, functional groups and the like that configure the crystal of a calcium phosphate (hereinafter, referred to as "ions and the like") are expressed using "a plurality of", such an expression means a plurality of ions of the same kind as the ions and the like in "the crystal of a calcium phosphate", and the ions and the like do not mean analogous kinds of different ions and the like.

FIG. 1 shows, among the unit lattices of the crystal of OCP, a portion corresponding to a $HPO_4$—OH layer (hydrated layer) seen in a c-axis direction. The c-axis direction is a direction perpendicular to both an a direction and a b direction that are indicated by arrows in the drawing.

The chemical composition formula of OCP containing no impurity is represented by $Ca_8(HPO_4)_2(PO_4)_4 \cdot 5H_2O$.

In FIG. 1, phosphate ions and hydrogen phosphate ions are indicated by triangular pyramids. Reference signs P1 to P6 are given to the individual phosphoric acids based on the difference in the chemical state. In FIG. 1, the largest sphere indicates a silver ion incorporated into the OCP crystal structure, and the second largest spheres indicate calcium ions.

The crystal of a calcium phosphate (OCP) of the present embodiment shown in FIG. 1 has an OCP crystal structure and is thus capable of exhibiting excellent biocompatibility and an excellent bone replacement property.

In addition, in the crystal of OCP according to the present embodiment, some of the plurality of calcium ions are replaced with at least silver ions. Therefore, the crystal of OCP is capable of exhibiting an antibacterial property due to the antibacterial property of the silver ions.

Even when the above-described silver ions are copper ions, the crystal of OCP exhibits an antibacterial property as in a case where some of the plurality of calcium ions are replaced with silver ions.

In the crystal of OCP of the present embodiment shown in FIG. 1, one of eight calcium ions in the portion corresponding to the $HPO_4$—OH layer is replaced with a silver ion. Since the ion radius of a calcium ion and the ion radius of a silver ion are close to each other, a silver ion is inserted into a position that has been originally occupied by a calcium ion. In the crystal of OCP shown in FIG. 1, a calcium ion in a conjugate relationship with P5 $PO_4$ is replaced with a silver ion.

In terms of the ion radius, a copper ion is not as close to a calcium ion as a silver ion, but a method to be described below makes it possible to insert a copper ion into a position that has been originally occupied by a calcium ion in the same manner as a silver ion.

OCP includes a hydroxyapatite layer, a transition layer and a hydrated layer in the unit lattices. The hydrated layer included makes it easy for a layer structure where a plurality of unit lattices overlaps one another to develop.

The different kinds of ions or other compositions that have been incorporated into the crystal of OCP where a layer structure has developed are strongly supported in the crystal structure compared with other calcium phosphates where a layer structure does not develop.

Here, "the different kinds of ions or other compositions" mean ions or compounds that are not included in the chemical composition formula of a corresponding calcium phosphate and, in the above-described embodiment, mean silver ions or copper ions.

In the case of using a bone substitute material made of the crystal of OCP where the different kinds of ions or other compositions are strongly supported, the different kinds of ions or other compositions are strongly held in the crystal of OCP in a liquid environment, but are released to the outside of the crystal little by little, that is, slowly released for the first time when receiving a lytic action of an osteoclast or the like. In addition, on the crystal surface of OCP, the different kinds of ions supported inside appear on the surface, and an antibacterial property is exhibited.

In a case where the different kinds of ions are silver ions or copper ions, these ions are supported by the same mechanism. Therefore, when the crystal of OCP according to the present embodiment is used as a material for a bone substitute material, an antibacterial property is held for a long period of time, and it is possible to expect effective suppression of the occurrence of postoperative infectious diseases.

When the different kinds of ions are added too much for the OCP crystal structure to be sustainable, it becomes impossible for the OCP crystal to hold the crystal structure. In order to detect whether or not OCP is contained in a sample, in a case where a clear peak is obtained at near 4.7° in the XRD pattern of the sample obtained by the powder X-ray diffraction method (XRD), it is possible to regard OCP as being contained in the measurement sample. In a case where a measurement sample contains a crystalline sample that is already known to show a clear peak at near 4.7° and is different from OCP, it is possible to detect OCP by confirming the presence of a peak having a clearly weaker peak intensity than a peak at 4.7° at near 9.2° in addition to the main peak.

The fact that some of calcium ions in OCP are replaced with different kinds of ions or other compositions can also be confirmed from, for example, the presence of the characteristic peaks of the ions or other compounds in XRD analysis. In a case where an ion that is inserted into the OCP crystal is a silver ion or a copper ion, the silver ion or the copper ion can be detected by confirming interlayer development from the intensity ratio between peaks in XRD analysis.

In addition, the insertion of the silver ion or the copper ion can be confirmed as, for example, a change in the vibration state of P5 $PO_4$ by an infrared spectroscopy (FT-IR). Furthermore, the insertion of the silver ion or the copper ion can be confirmed by detecting the silver ion or the copper ion by inductively coupled plasma atomic emission spectroscopy (ICP-AES).

The amount of a cation supported by a P5 $PO_4$ conjugation site in an OCP sample can be evaluated by evaluating the peak intensities at 4.7° and at 9.2° in the XRD pattern of the OCP sample.

That is, the integral intensity of the peak at 4.7° is represented by $I_{4.7}$, the integral intensity of the peak at 9.2° is represented by $I_{9.2}$, and each value is assigned to the following formula (1), thereby obtaining a relative intensity R.

$$R=I_{4.7}/I_{9.2} \quad (1)$$

The amount of a cation supported by the P5 $PO_4$ conjugation site can be regarded as increasing as the intensity of R increases.

The crystal of OCP can be prepared by a method for producing a powder having the crystal of OCP, a method for producing a compact having the crystal of OCP, which will be described below, or the like.

FIG. 2 is a schematic view of the crystal structure of another calcium phosphate (HAp) according to the first embodiment shown in the same format as in FIG. 1. FIG. 2 shows the unit lattices of the crystal of HAp seen in the C direction. The C direction is a direction perpendicular to both an a direction and a b direction that are indicated by arrows in the drawing.

The chemical composition formula of HAp containing no impurity is represented by $Ca_{10}(PO_4)_6(OH)_2$.

In the crystal of HAp of the present embodiment shown in FIG. 2, one of 10 calcium ions is replaced with a different kind of ion. When the ion radius of a calcium ion and the ion radius of the different kind of ion are close to each other, it becomes easy for the different kind of ion to be inserted into a position that has been originally occupied by a calcium ion. In the crystal of HAp shown in FIG. 2, a calcium ion in a conjugate relationship with $PO_4$ that is conjugated with a hydroxyl group is replaced with the different kind of ion.

Examples of the different kind of ion that replaces a calcium ion of HAp include a silver ion and a copper ion.

The different kinds of ions or other compositions incorporated into the crystal of HAp are supported in the crystal structure.

The crystal structure of a calcium phosphate can be confirmed from, for example, the presence of a characteristic peak of each crystal at near 10.5° in XRD analysis as in the case of OCP.

The fact that some of calcium ions in Ap are replaced with different kinds of ions or other compositions can also be confirmed from, for example, the presence of the characteristic peaks of the ions or other compounds in XRD analysis.

In addition, the insertion of the different kind of ion can be confirmed as, for example, a change in the vibration state of a hydroxyl group or a phosphate group by an infrared spectroscopy (FT-IR). Furthermore, the different kind of ion can also be detected by inductively coupled plasma atomic emission spectroscopy (ICP-AES).

The crystal of HAp, $CO_3Ap$ or the like can be prepared by a method for producing a powder having the crystal of a calcium phosphate, a method for producing a compact having the crystal of a calcium phosphate, which will be described below, or the like.

Hereinafter, several variations of the crystal of a calcium phosphate according to the first embodiment will be described as Embodiments 1-1 to 1-4.

Embodiment 1-1

In a crystal of a calcium phosphate according to Embodiment 1-1, a part of a plurality of calcium ions in the crystal structure of the calcium phosphate are replaced with silver ions or copper ions.

The content rate of the silver atom or the copper atom in the crystal of the calcium phosphate according to the present embodiment may be 0.01 atom % or more and 13.00 atom % or less.

In the crystal of a calcium phosphate according to the present embodiment, the silver ion or the copper ion is supported in the crystal of the calcium phosphate, and the crystal exhibits an antibacterial property in the case of being used as a material for bone substitute materials.

In a case where the calcium phosphate is OCP, since the silver ion or the copper ion is strongly supported in the crystal of OCP, in a case where the crystal is used as a material for bone substitute materials, the silver ion is slowly released for a long period of time. As a result, the antibacterial property is held for a long period of time, and it is possible to effectively suppress the occurrence of postoperative infectious diseases.

While not particularly limited, a preferable content rate of a silver atom or a copper atom is 0.1 atom % or more and 10 atom % or less, more preferably 1 atom % or more and 7 atom % or less and still more preferably 2 atom % or more and 5 atom % or less.

When the content rate of the silver atom is 0.001 atom % or more and 6.5 atom % or less, it is possible to suppress the surfaces of filler materials being tinged with a black or blue color due to the deposition or the like of a silver salt or a copper salt, and it is possible to suppress an aesthetic property, which is required at the time of using the crystal in the oral surgery field, being impaired.

The content of a silver element and a copper element in the crystal of the calcium phosphate can be measured by measuring the concentrations of Ca, $PO_4$, Ag and Cu in a solution containing a sample dissolved in 1% $HNO_3$ by inductively coupled plasma atomic emission spectroscopy (ICP-AES) and obtaining the proportions.

In addition, the content of the silver element and the copper element in the crystal of the calcium phosphate can also be measured by the solid-state nuclear magnetic resonance method (solid-state NMR method).

The crystal of OCP according to the present embodiment may be represented by a chemical composition formula $Ca_{8-a}Ag_b(PO_4)_4(HPO_4)_{2+x}\cdot 5H_2O$ or $Ca_{8-a}Cu_b(PO_4)_4(HPO_4)_{2+x}\cdot 5H_2O$, in the chemical composition formula, a may satisfy $0.00125 \leq a \leq 1.00$, b may satisfy $0.00125 \leq b \leq 1.00$, x may satisfy $0.00125 \leq x \leq 1.00$, and the a, the b and the x may be set such that the total of the valences of a calcium ion, a silver ion or a copper ion, a phosphate ion and a hydrogen phosphate ion in the chemical composition formula becomes zero.

While not particularly limited, in this case, a, b and x each may preferably satisfy $0.1 \leq a \leq 1.00$, $0.2 \leq b \leq 1.00$ and $0.2 \leq x \leq 1.00$, more preferably satisfy $0.3 \leq a \leq 1$, $0.6 \leq b \leq 1.00$ and $0.6 \leq x \leq 1.00$ and still more preferably satisfy $0.4 \leq a \leq 1$, $0.8 \leq b \leq 1.00$ and $0.8 \leq x \leq 1.00$.

The stoichiometric proportions in the chemical composition formula can be acquired from the results obtained by, for example, completely dissolving a crystal, which is a measurement subject, in 2% nitric acid and then measuring the concentrations of Ca, $PO_4$ and Ag in the solution by inductively coupled plasma atomic emission spectroscopy (ICP-AES).

The above-described method will be also true even in Embodiments 1-2 to 1-4 to be described below.

Embodiment 1-21

In a crystal of OCP according to Embodiment 1-2, a part of a plurality of calcium ions in the crystal structure of OCP are replaced with silver ions or copper ions, and, furthermore, another part of the plurality of calcium ions in the crystal structure of OCP are replaced with cations excluding a silver ion, a copper ion and a calcium ion.

Examples of the cations excluding a silver ion, a copper ion and a calcium ion include monovalent, divalent, trivalent, tetravalent or higher cations excluding a silver ion, a copper ion and a calcium ion, and examples thereof include alkali metal ions such as a sodium ion, a lithium ion and a potassium ion, alkaline earth metal ions such as a beryllium ion, a magnesium ion and a strontium ion, transition metal ions such as an iron ion, a manganese ion, a titanium ion, a zirconium ion, a scandium ion, a gold ion, a tin ion and a zinc ion, onium ions such as an ammonium ion, a phosphonium ion and a sulfonium ion and molecular ions such as a pyridinium ion and a tris-aminomethane ion.

Sodium ions incorporated in an appropriate quantity have an effect on promoting the development of a layer structure of the OCP crystal. Therefore, when sodium ions are inserted into the crystal structure of OCP as the cations excluding a silver ion, a copper ion and a calcium ion, the silver ions and the copper ions inserted into the crystal of OCP are more strongly supported in the OCP crystal.

As a result, the property of the silver ions and the copper ions being slowly released from bone substitute materials having the crystal of OCP further improves, and it is possible to impart an antibacterial property to bone substitute materials for a longer period of time.

The content rate of the silver atom or the copper atom in the crystal of OCP according to the present embodiment may be 0.01 atom % or more and 13.00 atom % or less.

While not particularly limited, a preferable content rate of a silver atom or a copper atom is 0.1 atom % or more and 10 atom % or less, more preferably 0.5 atom % or more and 9 atom % or less and still more preferably 1 atom % or more and 7 atom % or less.

Similar to the case of Embodiment 1-1, when the content rate of the silver atom or the copper atom is 0.001 atom % or more and 6.5 atom % or less, it is possible to suppress the surfaces of filler materials being tinged with a black or blue color due to the deposition or the like of a silver salt or a copper salt, and it is possible to suppress an aesthetic property, which is required at the time of using the crystal in the oral surgery field, being impaired.

The crystal of OCP according to the present embodiment may be represented by a chemical composition formula $Ca_{8-a}Ag_bX_c(PO_4)_4(HPO_4)_{2+x}\cdot 5H_2O$ or $Ca_{8-a}Cu_bX_c(PO_4)_4(HPO_4)_{2+x}\cdot 5H_2O$, X represents the cations excluding a silver ion, a copper ion and calcium ion and is monovalent, divalent, trivalent or tetravalent cations, in the chemical composition formula, a may satisfy $0.00125 \le a \le 1.00$, b+c may satisfy $0.00125 \le b+c \le 1.00$, b may satisfy $0.00125 \le b \le 1.00$, c may satisfy $0<c$, x may satisfy $0.00125 \le x \le 1.00$, and the a, the b and the x may be set such that the total of the valences of a calcium ion, a silver ion or a copper ion, a phosphate ion and a hydrogen phosphate ion in the chemical composition formula becomes zero.

While not particularly limited, in this case, a, b, a+b and x may preferably satisfy $0.1 \le a \le 1$, $0.2 \le b \le 1.00$, $0.2 \le b+c \le 1.00$ and $0.2 \le x \le 1.00$, more preferably satisfy $0.3 \le a \le 1.00$, $0.6 \le b \le 1.00$, $0.6 \le b+c \le 1.00$ and $0.6 \le x \le 1.00$ and still more preferably satisfy $0.4 \le a \le 1.00$, $0.8 \le b \le 1.00$, $0.8 \le b+c \le 1.00$ and $0.8 \le x \le 1.00$

Embodiment 1-3

In a crystal of OCP according to the present embodiment, a part of a plurality of calcium ions in the crystal structure of OCP are replaced with silver ions or copper ions, another part of the plurality of calcium ions in the crystal structure of OCP are replaced with cations excluding a silver ion, a copper ion and a calcium ion, and, furthermore, a plurality of phosphate ions or a plurality of hydrogen phosphate ions in the crystal structure of OCP are replaced with anions excluding a phosphate ion and anions excluding a hydrogen phosphate ion.

Examples of the anions excluding a phosphate ion and the anions excluding a hydrogen phosphate ion include monovalent, divalent or trivalent anions excluding a phosphate ion and a hydrogen phosphate ion, and examples thereof include dicarboxylic acid ions such as a carbonate ion, a borate ion, a sulfate ion, a silicate ion, a citrate ion, a succinate ion, a thiophosphate ion, a sebacate ion and an aspartate ion and molecular ion classified into bisphosphonate such as an etidronate ion.

The content rate of the silver atom or the copper atom in the crystal of OCP according to the present embodiment may be 0.01 atom % or more and 13.00 atom % or less.

While not particularly limited, a preferable content rate of a silver atom or a copper atom is 0.1 atom % or more and 10 atom % or less, more preferably 1 atom % or more and 7 atom % or less and still more preferably 2 atom % or more and 5 atom % or less.

Similar to Embodiment 1-1, when the content rate of the silver atom or the copper atom is 0.001 atom % or more and 6.5 atom % or less, it is possible to suppress the surfaces of filler materials being tinged with a black or blue color due to the deposition or the like of a silver salt or a copper salt, and it is possible to suppress an aesthetic property, which is required at the time of using the crystal in the oral surgery field, being impaired.

The crystal of OCP according to the present embodiment may be represented by a chemical composition formula $Ca_{8-a}Ag_bX_c(PO_4)_4(HPO_4)_{2+x}Zm\cdot 5H_2O$ or $Ca_{8-a}Cu_vX_c(PO_4)_4(HPO_4)_{2+x}Zm\cdot 5H_2O$, X represents the cations excluding a silver ion, a copper ion and calcium and is monovalent, divalent, trivalent or tetravalent cations, Z represents the anions excluding a phosphate ion or the anions excluding a hydrogen phosphate ion and is monovalent, divalent or trivalent anions, $m<6+x$ may be satisfied, in the chemical composition formula, a may satisfy $0.00125 \le a \le 1.00$, b+c may satisfy $0.00125 \le b+c \le 1.00$, x may satisfy $0.00125 \le x \le 1.00$, and the a, the b, the c, the x and the m may be set such that the total of the valences of a calcium ion, a silver ion, a copper ion, a phosphate ion, a hydrogen phosphate ion, the X and the Z in the chemical composition formula becomes zero.

While not particularly limited, in this case, a, b+c and x may preferably satisfy $0.1 \le a \le 1.00$, satisfy $0.2 \le b+c \le 1.00$ and satisfy $0.2 \le x \le 1.00$ and may more preferably satisfy $0.4 \le a \le 1.00$, satisfy $0.8 \le b+c \le 1.00$ and satisfy $0.8 \le x \le 1.00$.

Embodiment 1-4

The crystal of OCP according to the present embodiment is the crystal of OCP according to any one of Embodiment 1-1 to Embodiment 1-3, in which one or more of $HPO_4$, $PO_4$ and $H_2O$ in the chemical composition formula are replaced with a first composition having a functional group that chemically bonds to calcium, and the first composition is supported in the crystal of OCP.

Examples of the functional group that chemically bonds to calcium include a hydroxyl group, a carboxyl group, a phosphate group, an amino group, a silanol group, a sulfo group, a hydroxyl group, a thiol group and the like.

As an example of the first composition, as a molecule having a carboxyl group, a substance that is classified into monocarboxylic acid, dicarboxylic acid, tricarboxylic acid, carboxylate thiol, halogenated carboxylic acid, amino acid, aromatic acid, hydroxy acid, sugar acid, nitrocarboxylic acid, polycarboxylic acid or the like, a derivative thereof and a substance obtained by polymerizing the above-described substances can be used. That is, examples thereof include acetic acid, propionic acid, butyric acid, formic acid, valeric acid, succinic acid, citric acid, mercaptoundecanoic acid, thioglycolic acid, asparagusic acid, α-lipoic acid, β-lipoic acid, dihydrolipoic acid, chloroacetic acid, malonic acid, aconitic acid, malic acid, oxalic acid, tartaric acid, malonic acid, glutaric acid, adipic acid, fumaric acid, maleic acid, oxaloacetic acid, α-ketoglutaric acid, oxalosuccinic acid, pyruvic acid, isocitric acid, α-alanine, β-alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, cysteine, hydroxyproline, o-phosphoserine, desmosine, novalin, octopine, mannobin, saccharopin, N-methylglycine, dimethylglycine, trimethylglycine, citrulline, glutathione, creatine, γ-aminobutyric acid, theanine, lactic acid, folinic acid, folic acid, pantothenic acid, benzoic acid, salicylic acid, o-phthalic acid, m-phthalic acid, p-phthalic acid, nicotinic acid, picolinic acid, gallic acid, mellitic acid, cinnamic acid, jasmonic acid, undecylenic acid, levulinic acid, idulonic acid, glucuronic acid, galacturonic acid, glyceric acid, gluconic acid, muramic acid, sialic acid, mannuronic acid, glycolic acid, glyoxylic acid, ethylenediaminetetraacetic acid (EDTA), nitroacetic acid, nitrohydrocinnamic acid, nitrobenzoic acid, polyacrylic acid, polycitric acid, polyitaconic acid, salts thereof and the like.

Examples of a molecule having a silanol group include γ-methacryloxypropyltrimethoxysilane (γ-MPTS), tetraethyl orthosilicate (TEOS), sodium silicate, orthosilicic acid, metasilicic acid, metadisilicic acid, salts thereof and the like.

Examples of a molecule having a phosphate group include adenosine triphosphate (ATP), adenosine diphosphate (ADP), nucleotide, glucose-6-phosphate, flavin mononucleotide, polyphosphoric acid, 10-methacryloyloxydecyl dihydrogen phosphate (MDP), phytic acid, etidronic acid, salts thereof and the like.

Examples of a molecule having a sulfo group include benzenesulfonic acid, taurine, linear sodium alkylbenzene sulfonate, xylene silanol, bromophenol blue, methyl orange, 4,4'-diisothiocyano-2,2'-stilbenedisulfonic acid (DIDS), azorubine, amaranth, indigo carmine, water blue, cresol red, coomassie brilliant blue, congo red, sulfanilic acid, tartrazine, thymol blue, tosyl azide, new coccine, pyranine, methylene blue, hydroxyethylpiperazine ethane sulfonic acid (HEPES), sodium cyclamate, saccharin, taurocholic acid, isethionic acid, cysteic acid, 10-camphorsulfonic acid, 4-hydroxy-5-aminonaphthalene-2,7-disulfonic acid, methanesulfonic acid, ethanesulfonic acid, salts thereof and the like.

Examples of a molecule having a hydroxyl group include compounds classified into alcohols, 2-hydroxyethyl methacrylate (HEMA), hydroxylamine, hydroxamic acid, phenol, compounds classified into aldol, compounds classified into sugars, compounds classified into glycols, inositol, compounds classified into sugar alcohols, pantetheine, salts thereof and the like.

Examples of a molecule having a thiol group include captopril, methanethiol, ethanethiol, cysteine, glutathione, thiophenol, acetylcysteine, 1,2-ethanedithiol, cysteamine, dithioerythritol, dithiothreitol, dimercaprol, thioglycolic acid, thiopronine, 2-naphthalenethiol, bucillamine, furan-2-ylmethanethiol, D-penicillamine, mycothiol, mesna, 3-methyl-2-butene-1-thiol, 3-mercaptopyruvic acid, salts thereof and the like.

The content rate of the silver atom or the copper atom in the crystal of OCP according to the present embodiment may be 0.01 atom % or more and 13.00 atom % or less.

While not particularly limited, a preferable content rate of a silver atom or a copper atom is 0.1 atom % or more and 10 atom % or less, more preferably 1 atom % or more and 7 atom % or less and still more preferably 2 atom % or more and 5 atom % or less.

Similar to Embodiment 1-1, when the content rate of the silver atom or the copper atom is 0.001 atom % or more and 6.5 atom % or less, it is possible to suppress the surfaces of filler materials being tinged with a black or blue color due to the deposition or the like of a silver salt or a copper atom, and it is possible to suppress an aesthetic property, which is required at the time of using the crystal in the oral surgery field, being impaired.

To numerical value ranges regarding the stoichiometry in the chemical composition formula in the present embodiment and preferable ranges thereof, it is possible to apply the respective descriptions of Embodiments 1-1 to 1-3.

Even in a case where the calcium phosphate is HAp, FAp, ClAp or $CO_3$Ap, similar to the case where the calcium phosphate is OCP, a part of a variety of ions that configure the crystal may be partially replaced with ions other than a silver ion and a copper ion as described in Embodiments 1-1 to 1-4.

Second Embodiment

"Powder Having Crystal of Replacement-Type Calcium Phosphate"

A second embodiment of the present invention is a powder having a crystal of a replacement-type calcium phosphate (hereinafter, referred to as "powder of a calcium phosphate"). The powder of OCP of the present embodiment is a powder having the crystal of a calcium phosphate of the first embodiment.

The grain diameter of the powder of a calcium phosphate of the present embodiment is preferably 0.05 μm to 100 μm, more preferably 0.5 μm to 20 μm and still more preferably 1 μm to 10 μm.

The content rate of the crystal of a calcium phosphate with respect to the powder of a calcium phosphate of the present embodiment is preferably 10 mass % to 100 mass %, more preferably 50 mass % to 100 mass % and still more preferably 75 mass % to 100 mass %.

The lower limit value of the above-described range may be 60, 70, 80 or 90 mass %.

The content rate of the crystal of a calcium phosphate with respect to the total mass of the powder of a calcium phosphate can be measured by the XRD method or the FT-IR method.

As substances other than the crystal of a calcium phosphate that are contained in the powder of a calcium phosphate of the present embodiment, for example, HAp (excluding a case where the calcium phosphate is the crystal of HAp), β-TCP, α-TCP, whitlockite, calcium hydrogen phosphate dihydrate (DCPD), calcium carbonate, calcium sulfate, gallium phosphate, magnesium phosphate and other inevitable impurities are contained.

These substances contained other than the crystal of a calcium phosphate are added to the powder of OCP mainly for improvement in the stability and easy handleability of the crystal of a calcium phosphate. The inevitable impurities are components that are inevitably incorporated at the time of producing the powder of a calcium phosphate.

Calcium carbonate and DCPD, which are the substances contained other than the crystal of a calcium phosphate, have an effect on new born formation improvement by the slow release of a Ca ion. α-TCP, DCPD and calcium sulfate have an effect on imparting a hardening property. HAp has an effect on a shaping-without-cutting property and a dissolution rate delay in living bodies. Examples of the inevitable impurities include silver phosphate, silver, silver oxide and the like, and the upper limit value of the content of the inevitable impurities differs with the content of the OCP crystal in the powder of a calcium phosphate. For example, in a case where the content rate of the crystal of a calcium phosphate is 100%, the upper limit value of the content of the inevitable impurities is 0.1 mass %. In a case where the content rate of the crystal of a calcium phosphate is 90%, 70% and 50%, the upper limit value is 0.9 mass %, 0.7 mass % and 0.5 mass %, respectively.

The powder of a calcium phosphate of the present embodiment can be used in a form of being injected into an affected area by, for example, being mixed with a liquid to be made into a paste.

In a case where the powder of a calcium phosphate of the present embodiment is used as a material for bone substitute materials, the bone substitute materials are capable of exhibiting excellent biocompatibility. In a case where the calcium phosphate is OCP, the bone substitute materials are capable of exhibiting an excellent bone replacement property.

In addition, since a part of a plurality of calcium ions in the crystal structure of the calcium phosphate has been replaced with silver ions or copper ions, the bone substitute materials are capable of exhibiting an antibacterial property.

In a case where the calcium phosphate is OCP, since a layer structure is developed and the silver ions or the copper ions are strongly supported in the crystal structure of OCP, the bone substitute materials are capable of exhibiting the antibacterial property for a long period of time and of effectively suppressing the occurrence of postoperative infectious diseases.

In addition, when the content of the silver ions that are inserted into the crystal of a calcium phosphate is set in an appropriate range, it is possible to suppress the surfaces of the filler materials being tinged with a black color attributed to the precipitation of a silver salt or the like. As a result, it is possible to suppress the aesthetic property, which is required at the time of using the powder in the oral surgery field, being impaired.

Third Embodiment

"Block Material Having Crystal of Replacement-Type Calcium Phosphate"

A third embodiment of the present invention is a block material having a crystal of a replacement-type calcium phosphate (hereinafter, referred to as "block material of a calcium phosphate"). The block material of the present embodiment is a block material having the crystal of a calcium phosphate of the first embodiment and can be used as, for example, a bone substitute material as it is or processed as required. Here, the block material means a material having a columnar shape such as a prism or a cylinder, a block shape or a massive shape.

The block material of a calcium phosphate of the present embodiment is hardened by a chemical bond of an inorganic component in the block material of a calcium phosphate or the entanglement or fusion of the crystals of the inorganic component. Therefore, the block material of a calcium phosphate of the present embodiment has a sufficient physical strength as bone substitute materials.

While not particularly limited, the compressive strength of the block material of a calcium phosphate of the present embodiment is preferably 2 MPa or more and more preferably 5 MPa or more. The upper limit value is not particularly limited, but becomes, substantially, 500 MPa or less.

In a case where the block material of a calcium phosphate of the present embodiment is used as a bone substitute material, the block material of a calcium phosphate has the crystal of the calcium phosphate and is thus capable of exhibiting excellent biocompatibility.

In a case where the calcium phosphate is OCP, the bone substitute materials are capable of exhibiting an excellent bone replacement property.

In addition, since a part of a plurality of calcium ions in the crystal structure of the calcium phosphate has been replaced with silver ions or copper ions, the bone substitute materials are capable of exhibiting an antibacterial property.

In a case where the calcium phosphate is OCP, since a layer structure is developed and the silver ions or the copper ions are strongly supported in the crystal structure of OCP, the bone substitute materials are capable of exhibiting the antibacterial property for a long period of time and of effectively suppressing the occurrence of postoperative infectious diseases.

In addition, when the content of the silver ions that are inserted into the crystal of a calcium phosphate is set in an appropriate range, it is possible to suppress the surfaces of the filler materials being tinged with a black color attributed to the precipitation of a silver salt or the like. As a result, it is possible to suppress the aesthetic property, which is required at the time of using the powder in the oral surgery field, being impaired.

The content rate of the crystal of a calcium phosphate with respect to the total mass and substances contained other than the crystal in the block material of a calcium phosphate are the same as in the second embodiment.

Fourth Embodiment

"Porous Material Having Replacement-Type Calcium Phosphate Crystal"

A fourth embodiment of the present invention is a porous material having a crystal of a replacement-type calcium phosphate (hereinafter, referred to as "porous material of a calcium phosphate"). The porous material of the present embodiment is a porous material having the crystal of a calcium phosphate of the first embodiment and can be used as, for example, a material for bone substitute materials.

The porous material of a calcium phosphate of the present embodiment is made of a porous material having the crystal of a calcium phosphate. In the porous material, an extremely large number of pores are formed. The pores form a three-dimensionally communicating pore structure and thus makes it easy for body tissues to intrude into the inside in a case where the calcium phosphate porous material is used as a bone substitute material. As a result, the porous material of a calcium phosphate of the present embodiment has superior biocompatibility and a superior bone replacement property compared with porous bodies that do not have any porous material structures.

While not particularly limited, the porosity of the porous material of a calcium phosphate of the present embodiment is preferably 10% or more and 95% and more preferably 50% or more and 90% or less.

In a case where the porous material of a calcium phosphate of the present embodiment is used as a material for bone substitute materials, the bone substitute materials are capable of exhibiting superior biocompatibility.

In a case where the calcium phosphate is OCR the bone substitute materials are capable of exhibiting an excellent bone replacement property.

In addition, since a part of a plurality of calcium ions in the crystal structure of the calcium phosphate has been replaced with silver ions or copper ions, the bone substitute materials are capable of exhibiting an antibacterial property.

In a case where the calcium phosphate is OCP, since a layer structure is developed and the silver ions or the copper ions are strongly supported in the crystal structure of OCP, the bone substitute materials are capable of exhibiting the antibacterial property for a long period of time and of effectively suppressing the occurrence of postoperative infectious diseases.

In addition, when the content of the silver ions that are inserted into the crystal of a calcium phosphate is set in an appropriate range, it is possible to suppress the surfaces of the filler materials being tinged with a black color attributed to the precipitation of a silver salt or the like. As a result, it is possible to suppress the aesthetic property, which is required at the time of using the powder in the oral surgery field, being impaired.

The content rate of the crystal of a calcium phosphate with respect to the total mass and substances contained other than the crystal in the porous material of a calcium phosphate are the same as in the second embodiment.

Fifth Embodiment

"Bone Substitute Material Having Replacement-Type Calcium Phosphate Crystal"

A fifth embodiment of the present invention is a bone substitute material.

The bone substitute material of the present embodiment is made of the powder of OCP of the second embodiment, the block material of the third embodiment or the porous material of the fourth embodiment having the crystal of a calcium phosphate of the first embodiment.

The use of the bone substitute material of the present embodiment makes it possible to obtain the technical effect that can be obtained in each of the above-described embodiments.

Sixth Embodiment

"Oral Bone Substitute Material Having Replacement-Type Calcium Phosphate Crystal"

A sixth embodiment of the present invention is an oral bone substitute material.

The oral bone substitute material of the present embodiment is made of the powder of OCP of the second embodiment, the block material of the third embodiment or the porous material of the fourth embodiment having the crystal of a calcium phosphate of the first embodiment.

The use of the oral bone substitute material of the present embodiment makes it possible to obtain the technical effect that can be obtained in each of the above-described embodiments.

Seventh Embodiment

"Method for Producing Crystal of Replacement-Type Calcium Phosphate"

A seventh embodiment of the present invention is a method for producing a crystal of a replacement-type calcium phosphate (hereinafter, referred to as "method for producing a crystal of a calcium phosphate").

Figure 3:
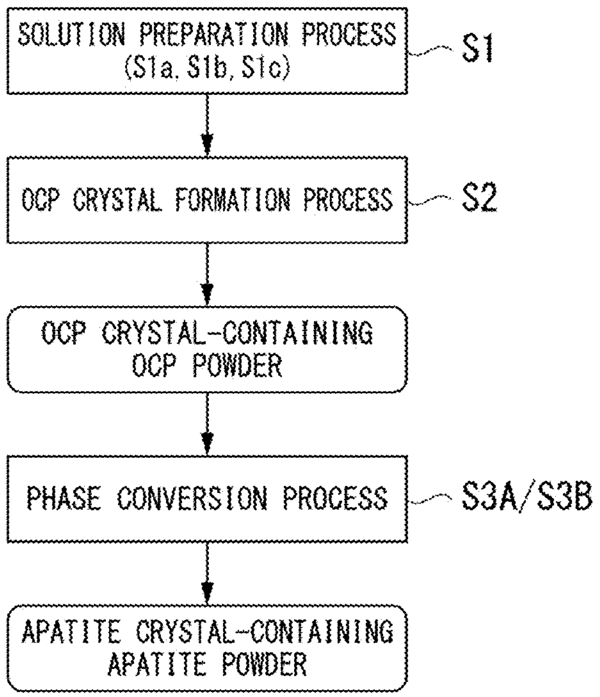
FIG. 3 is a flowchart showing process of a method for producing a crystal of a calcium phosphate according to a seventh embodiment of the present invention.

FIG. 3 is an example of the method for producing a crystal of a calcium phosphate according to the seventh embodiment of the present invention and a flowchart showing process of a method for producing a crystal of replacement-type OCP and a crystal of replacement-type Ap.

The method for producing an OCP crystal includes a process of dissolving a silver-containing composition or a copper-containing composition in a solvent containing water to prepare a solution containing a complex ion of a silver ion or a copper ion (solution preparation process S1) and a process of adding a compound containing phosphoric acid, hydrogen and calcium to the solution to form an octacalcium phosphate-based crystal (OCP crystal formation process S2), and a part of a plurality of calcium ions in the structure of the crystal of OCP are replaced with silver ions or copper ions.

[Solution Preparation Process S1]

In the solution preparation process S1, a solution containing a complex ion in which a ligand forms a coordination bond with a silver ion or a copper ion is prepared by a complex ion formation reaction.

A solvent of the solution may be water or a liquid mixture of water and an organic solvent. For example, the solvent may be water containing 0.01% to 99.99% of an alcohol. Examples of the organic solvent include monovalent alcohols including primary alcohols such as methanol, ethanol, propan-1-ol, butan-1-ol, pentan-1-ol, hexan-1-ol, heptan-1-ol, octan-1-ol, nonan-1-ol and decan-1-ol, secondary alcohols such as 2-propanol (isopropyl alcohol), butan-2-ol, pentan-2-ol, hexan-2-ol and cyclohexanol and tertiary alcohols such as tert-butyl alcohol, 2-methylbutan-2-ol, 2-methylpentan-2-ol, 2-methylhexan-2-ol, 3-methylpentan-3-ol and 3-methyloctan-3-ol, divalent alcohols such as ethylene glycol and diethylene glycol, trivalent alcohols such as glycerin, aromatic ring alcohols such as phenol, polyethers such as polyethylene glycol (PEG) and polypropylene glycol (PPG), polycarboxylic acids such as polyacrylic acid and polycarbamyl phosphate, aliphatic acids such as acetic acid, valeric acid, caproic acid, lauric acid, palmitic acid, stearic acid, oleic acid and linoleic acid, alkanes such as pentane, butane, hexane, septane and octane, ethers such as dimethyl ether, methyl ethyl ether and diethyl ether, aromatic compounds such as benzene, toluene, picric acid and TNT, polycyclic aromatic hydrocarbons such as naphthalene, azulene and anthracene, organic halogen compounds such as chloromethane, dichloromethane, chloroform and carbon tetrachloride, esters such as ethyl acetate, methyl butyrate, methyl salicylate, ethyl formate, ethyl butyrate, ethyl caproate, octyl acetate, dibutyl phthalate, ethylene carbonate and ethylene sulfide, cycloalkanes such as cyclopentane, cyclohexane and dekalin, ketones such as bicycloalkane, acetone, methyl ethyl ketone and diethyl ketone, aldehydes such as formaldehyde, acetaldehyde, propionaldehyde, butanal, pentanal, hexanal and vanillin, amine compounds such as aminomethane, aminoethane, ethylenediamine, triethylamine and aniline, sugars such as glucose, fructose and threitol, thiols such as methanethiol, ethanethiol, propanethiol and thiophenol, disulfide compounds such as dimethylsulfide, diphenylsulfide, asparagusic acid, cystamine and cystine and the like. These organic solvents may be used singly or a plurality of organic solvents may be mixed and used.

A compound that serves as a silver ion source or a copper ion source is added to the solvent. As the silver ion source, it is possible to use silver nitrate, silver sulfate, silver fluoride and the like, which are easily-soluble silver compounds. As the copper ion source, it is possible to use copper nitrate trihydrate, copper chloride, copper acetate, copper sulfate, copper bromide, copper iodide, copper iodate, copper fluoride and the like, which are easily-soluble copper compounds.

Furthermore, a compound that serves as a ligand source that forms a coordinate bond with a silver ion or a copper ion is added to the solvent. As the ligand source, it is possible to use an ammonium salt, a pyridinium salt, a saccharin salt and the like.

The silver ion source or the copper ion source and the ligand source are added to the solvent and then stirred under predetermined conditions to dissolve these.

Ordinarily, silver salts and copper salts are poorly soluble and are often precipitated as insoluble salts in high-concentration solutions under weakly basic conditions. However, when a silver ion or a copper ion and a ligand that coordinates with a silver ion or a copper ion coexist in a solution, a complex ion is formed, and the precipitation of a silver salt or a copper salt in a solution containing a high concentration of a silver ion or a copper ion can be suppressed.

The formation of the complex ion of the silver ion or the copper ion makes it possible to obtain a colorless and transparent solution even when the silver ion concentration or the copper ion concentration is high.

For example, silver nitrate may be used as the silver ion source, and copper nitrate trihydrate may be used as the copper ion source. The solution may be prepared using ammonium hydrogen phosphate as the ligand source and pure water as the solvent.

In this case, the concentrations of the silver nitrate and the copper nitrate may be set within a range of 0.0001 mol/L to 0.2 mol/L and preferably set within a range of 0.001 mol/L to 0.05 mol/L.

In addition, the concentration of the ammonium hydrogen phosphate may be set within a range of 0.01 mol/L to 2 mol/L and preferably set within a range of 0.1 mol/L to 2 mol/L.

In order to obtain a transparent solution, silver nitrate or copper nitrate trihydrate and ammonium hydrogen phosphate are added to the solvent and then stirred in an airtight container at a temperature within 0° C. to 99° C.

The solution preparation process S1 may include a process Sla of dissolving a second composition containing a cation excluding a silver ion or a copper ion and a calcium ion in the solvent.

As the second composition, it is possible to use a substance that turns into a water-soluble cation such as a sodium ion, a potassium ion or a rubidium ion.

The concentration of the second composition may be set within a range of 0 mol/L to 5 mol/L, preferably set within a range of 0.01 mol/L to 2 mol/L and more preferably set within a range of 0.5 mol/L to 2 mol/L.

The solution preparation process S1 may include the process S1a of dissolving the second composition in the solvent and a process S1b of dissolving a third composition containing an anion excluding a phosphate ion or an anion excluding a hydrogen phosphate ion in the solvent.

As the third composition, it is possible to use a carbonate ion, a phosphate ion, a sulfate ion, a silicate ion, a citrate ion, a succinate ion and the like.

The concentration of the third composition may be set within a range of 0 mol/L to 2 mol/L and preferably set within a range of 0.01 mol/L to 0.5 mol/L.

The solution preparation process S1 may include a process S1c of dissolving a fourth composition containing a functional group that chemically bonds to calcium in the solvent.

As the fourth composition, it is possible to use polyacrylic acid, inositol hexaphosphate, nucleic acid and the like.

The concentration of the fourth composition may be set within a range of 0 mol/L to 1 mol/L and preferably set within a range of 0.01 mol/L to 0.1 mol/L.

The concentration of the silver ion, the concentration of the copper ion or the total concentration of the silver ion and the copper ion in the solution preparation process S1 may be in a range of 0.1 mmol/L to 200 mmol/L and preferably in a range of 2.5 mmol/L to 30 mmol/L.

[OCP Crystal Formation Process S2]

In the OCP crystal formation process S2, a compound containing phosphoric acid, hydrogen and calcium is added to the solution, and a crystal of OCP in which a part of calcium ions in the crystal structure of OSP have been replaced with the silver ions or the copper ions is formed.

Phosphoric acid, hydrogen and calcium may be added as one kind of compound or may be added as a plurality of kinds of compounds. In the case of being added as one kind of compound, it is possible to use calcium hydrogen phosphate dihydrate (DCPD), calcium monohydrogen phosphate (anhydrous) (DCPA) and the like.

As phosphoric acid, hydrogen and calcium, it is possible to use powder-form compounds.

The total amount of the compound containing phosphoric acid, hydrogen and calcium added may be within a range of 0.1 g to 85 g and more preferably within a range of 0.5 g to 15 g with respect to 100 mL of the solution.

The compound containing phosphoric acid, hydrogen and calcium is added and stirred and then reacted at a predetermined temperature for a predetermined time in order to promote the formation of the OCP crystal structure.

For example, in the case of using DCPD, the compound is reacted at a temperature within a range of 0° C. to 99° C. for a time within a range of 0.1 hours to 168 hours.

During this reaction, an OCP-based crystal in which a part of calcium ions in the crystal structure of OSP have been replaced with silver ions or copper ions is formed.

After the reaction, the obtained precipitate is collected, washed with pure water and dried, whereby a crystal of OCP in which a part of calcium ions in the crystal structure of OSP have been replaced with silver ions or copper ions can be obtained.

As shown in the flowchart of FIG. 3, the obtained crystal of replacement-type OCP is further subjected to phase conversion process S3A and S3B to be described below, whereby a crystal of replacement-type Ap can be obtained.

[Phase Conversion Process S3A]

In the phase conversion process S3A, the phase of the crystal of OCP is converted to a crystal of HAp while maintaining the solid state by hydrolysis or a hydrothermal reaction in a phase conversion solution.

Here, the hydrolysis that is carried out during the phase conversion means a reaction in which a calcium phosphate, which is a thermodynamically metastable phase, including OCP, is immersed in water or a solution, and water or this solution and the calcium phosphate are brought into contact with each other, whereby a part of molecules that are contained in the calcium phosphate are released into the solution, a part of molecules that are contained in the solution are incorporated, or both reactions am caused at the same time, thereby changing the composition and the crystal structure of the calcium phosphate to change the calcium phosphate to a more thermodynamically stable compound.

Here, the hydrothermal reaction that is carried out during the phase conversion means a treatment in which a solution and a calcium phosphate sample are enclosed in a pressure-resistant airtight container under a temperature condition under which the solution boils in an open system, thereby reading the solution with the calcium phosphate in a solution state without gasifying the solution. The reaction temperature is freely set depending on the composition in hot water in this case.

The temperature condition in the hydrothermal reaction is not particularly limited. Normally, the temperature is −80° C. or higher and 350° C. or lower, preferably 0° C. or higher, more preferably 25° C. or higher and particularly preferably 100° C. or higher.

The phase conversion solution that is used in the hydrolysis reaction is not particularly limited. Normally, the phase conversion solution is water and an aqueous solution. In addition to these, examples thereof include monovalent alcohols including primary alcohols such as methanol, ethanol, propan-1-ol, butan-1-ol, pentan-1-ol, hexan-1-ol, heptan-1-ol, octan-1-ol, nonan-1-ol and decan-1-ol, secondary alcohols such as 2-propanol (isopropyl alcohol), butan-2-ol, pentan-2-ol, hexan-2-ol and cyclohexanol and tertiary alcohols such as tert-butyl alcohol, 2-methylbutan-2-ol, 2-methylpentan-2-ol, 2-methylhexan-2-ol, 3-methylpentan-3-ol and 3-methyloctan-3-ol, divalent alcohols such as ethylene glycol and diethylene glycol, trivalent alcohols such as glycerin, aromatic ring alcohols such as phenol, polyethers such as polyethylene glycol (PEG) and polypropylene glycol (PPG), polycarboxylic acids such as polyacrylic acid and polycarbamyl phosphate, aliphatic acids such as acetic acid, valeric acid, caproic acid, lauric acid, palmitic acid, stearic acid, oleic acid and linoleic acid, alkanes such as pentane, butane, hexane, septane and octane, ethers such as dimethyl ether, methyl ethyl ether and diethyl ether, aromatic compounds such as benzene, toluene, picric acid and TNT, polycyclic aromatic hydrocarbons such as naphthalene, azulene and anthracene, organic halogen compounds such as chloromethane, dichloromethane, chloroform and carbon tetrachloride, esters such as ethyl acetate, methyl butyrate, methyl salicylate, ethyl formate, ethyl butyrate, ethyl caproate, octyl acetate, dibutyl phthalate, ethylene carbonate and ethylene sulfide, cycloalkanes such as cyclopentane, cyclohexane and dekalin, ketones such as bicycloalkane, acetone, methyl ethyl ketone and diethyl ketone, aldehydes such as formaldehyde, acetaldehyde, propionaldehyde, butanal, pentanal, hexanal and vanillin, amine compounds such as aminomethane, aminoethane, ethylenediamine, triethylamine and aniline, sugars such as glucose, fructose and threitol, thiols such as methanethiol, ethanethiol, propanethiol and thiophenol, disulfide compounds such as dimethylsulfide, diphenylsulfide, asparagusic acid, cystamine and cystine and the like. These phase conversion solutions may be used singly or a plurality of phase conversion solutions may be mixed and used.

The crystal of OCP is prepared by causing the hydrolysis reaction of the crystal of OCP in the phase conversion solution for the hydrolysis reaction at a temperature in a range of −80° C. to 300° C. normally for 10 minutes to 30 days, preferably for two hours to 14 days and more preferably for two hours to seven days.

A powder of HAp containing the crystal of HAp that is obtained by the phase conversion process S3A is washed with distilled water several times and then heated and dried at 80° C. for one day.

Due to the hydrolysis reaction, water molecules in the OCP-based crystal are removed, and the hydrated layer (water-containing layer) disappears. In addition, it is considered that, in the OCP-based crystal structure, a part of the crystal lattices shifts in a b-axis direction and, consequently, the phase conversion of the OCP crystal structure to the Hp crystal structure occurs.

The phase conversion solution that is used in the hydrothermal reaction is normally water and an aqueous solution, but the above-described phase conversion solution that is used in the hydrolysis reaction can be used as necessary.

The crystal of OCP is subjected to the hydrothermal reaction in the phase conversion solution for the hydrothermal reaction at a temperature in a range of 100° C. to 300° C. for 10 minutes to 30 days.

The other conditions are the same as those in the case of the hydrolysis reaction.

Regardless of which one of the hydrolysis reaction and the hydrothermal reaction is carried out in the phase conversion process S3A, the water molecules in the OCP-based crystal are removed, and the hydrated layer (water-containing layer) disappears. In addition, it is considered that, in the crystal structure of OCP, a part of the crystal lattices shifts in a b-axis direction and, consequently, the phase conversion of the OCP crystal structure to the HAp crystal structure occurs.

Almost all of the silver ions or the copper ions inserted into the crystal of replacement-type OCP that has been used as a starting material in the phase conversion process S3A are held in the crystal of replacement-type HAp even after the phase conversion process S3A.

[Phase Conversion Process S3B]

In the phase conversion process S3B, the phase of the crystal of OCP is converted to a crystal of $CO_3Ap$ while maintaining the solid state by a carbonation treatment in a phase conversion solution.

Here, the carbonation treatment that is carried out during the phase conversion means a treatment in which a solution containing carbonic acid, a solution containing a substance that decomposes or the like in a reaction environment to release carbonate ions or a suspension and a calcium phosphate are brought into contact with each other to incorporate the carbonate ions into the calcium phosphate.

As the phase conversion solution that is used in the carbonation treatment, it is possible to use solutions of a carbonate such as a $(NH_4)_2CO_3$ solution, a sodium hydrogen carbonate solution, a sodium carbonate solution, a potassium hydrogen carbonate solution, a potassium carbonate solution, a rubidium carbonate solution and a lithium carbonate solution, organic salt solutions that decompose under a heating environment and release carbonate ions such as a citric acid solution and a sodium citrate solution, liquefied carbon dioxide and the like.

The crystal of OCP is subjected to a hydrolysis reaction in the phase conversion solution for the carbonation treatment at a temperature in a range of −80° C. to 350° C. for 10 minutes to 30 days.

A powder of $CO_3Ap$ containing the crystal of $CO_3Ap$ that is obtained by the phase conversion process S3B is washed with distilled water several times and then heated and dried at 80° C. for one day.

In the case of the phase conversion process S3B as well, it is considered that the phase conversion from the OCP crystal structure to the $CO_3Ap$ crystal structure occurs by the same mechanism as in the case of the phase conversion process S3A.

Almost all of the silver ions or the copper ions inserted into the crystal of replacement-type OCP that has been used as a starting material in the phase conversion process S3B are held in the crystal of replacement-type HAp even after the phase conversion process S3B.

Eighth Embodiment

"Method for Producing Block Material of Replacement-Type Calcium Phosphate Crystal"

An eighth embodiment of the present invention is a method for producing a block material in which a part of a plurality of calcium ions in the structure of the crystal of any one calcium phosphate selected from the group consisting of OCP, HAp, FAp, ClAp and $CO_3Ap$ are replaced with silver ions or copper ions.

Figure 4:
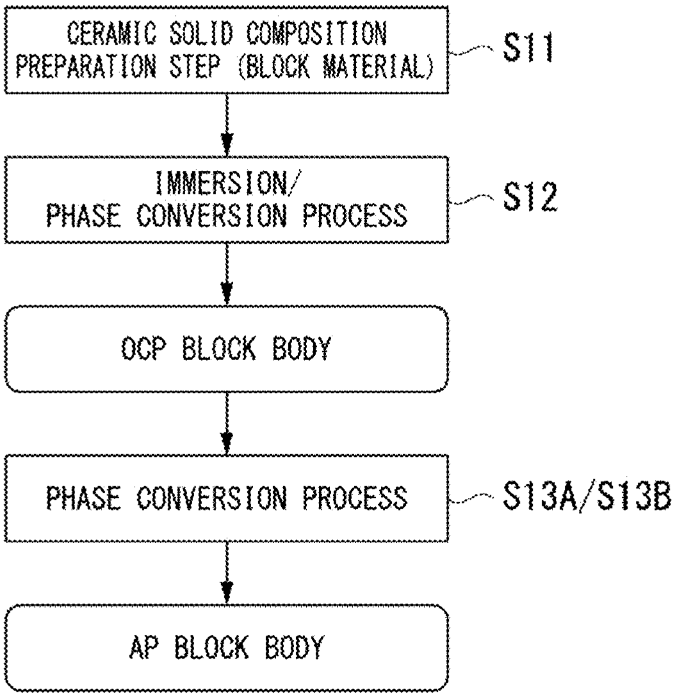
FIG. 4 is a flowchart showing process of a method for producing a block material of a calcium phosphate according to an eighth embodiment of the present invention.

FIG. 4 is a flowchart showing process of the method for producing a block material of a calcium phosphate according to the eighth embodiment of the present invention.

The method for producing a block material of the present embodiment includes a ceramic solid composition preparation process S11 of preparing a solid composition (block material) made of ceramic containing at least one of calcium and phosphoric acid and a process S12 of immersing the solid composition in a solution containing the other of calcium and phosphoric acid and either or both of a silver ion or a complex ion of silver and a copper ion or a complex ion of copper and converting the solid composition to an octacalcium phosphate-based crystal to obtain a block material, in which the block material is hardened by a chemical bond of an inorganic component in the block material or the entanglement or fusion of the crystals of the inorganic component, and a part of a plurality of calcium ions in the structure of the octacalcium phosphate-based crystal are replaced with silver ions or copper ions.

In the method for producing a block material of the present embodiment, for example, a solid composition made of ceramic containing at least one of calcium and phosphoric acid (precursor ceramic block) is immersed in a solution containing the other of calcium and phosphoric acid and either or both of a silver ion or a complex ion of silver and a copper ion or a complex ion of copper, and the solid composition is converted to a crystal of OCR

[Immersion/Phase Conversion Process S12]

In the immersion/phase conversion process S12, a solid composition made of ceramic containing at least one of calcium and phosphoric acid is immersed in a solution containing the other of calcium and phosphoric acid and either or both of a silver ion or a complex ion of silver and a copper ion or a complex ion of copper, and the solid composition is converted to an octacalcium phosphate-crystal to obtain a block material.

As the solid composition, it is possible to use a hardened body of DCPA. The hardened body of DCPA can be made by, for example, the following procedure.

β-TCP and monocalcium phosphate monohydrate (MCPM: $Ca(H_2PO_4)_2 \cdot H_2O$) are mixed in a state of holding the dry state to obtain a brushite cement powder. In order to prevent deterioration by moisture absorption, the obtained brushite cement powder is stored at, for example, 60° C.

The brushite cement powder is packed into a mold, 70% ethanol is added dropwise, and then a compression pressure is applied from the outside to carry out primary hardening. The primary hardening is completed by curing the brushite cement powder for 24 hours or longer while holding the compressed state, for example, under conditions of a humidity of 100% and 40° C.

The hardened body after the primary hardening obtained as described above is relieved from the compression pressure and then exposed again, for example, under conditions of a humidity of 100% and 40° C. for 24 hours or longer, whereby a ceramic solid composition (DCPA hardened body), which serves as a ceramic block of a precursor, can be obtained.

The solid composition made of ceramic containing at least one of calcium and phosphoric acid, which can be obtained by the above-described method, is immersed in a solution containing the other of calcium and phosphoric acid and either or both of a silver ion or a complex ion of silver and a copper ion or a complex ion of copper in the immersion/phase conversion process S12.

For example, in a case where the DCPA hardened body is used as the ceramic solid composition, the DCPA hardened body is immersed in a solution mixture containing 0.1 mol/L to 2 mol/L ammonium hydrogen phosphate, 0.1 mol/L to 200 mol/L silver nitrate and 0 mol/L to 5 mol/L sodium nitrate at a predetermined temperature for a predetermined time.

The solution mixture contains a complex ion in which ammonium coordinates with a silver ion or a copper ion.

The temperature condition is preferably 0° C. to 99° C. and more preferably 35° C. to 85° C.

The immersion time is preferably 0.5 days to 14 days and more preferably one day to seven days.

In a case where the precipitation of a silver salt in the prepared solution is observed, 0 mol/L to 5 mol/L ammonium nitrate may be further added thereto as an ammonium ion source for forming a complex ion of silver or copper.

While the ceramic solid composition is being immersed in the solution, DCPA is converted to OCP. Furthermore, the silver ions present in the immersion solution in a complex ion state are incorporated into the OCP crystal structure and inserted in a manner of replacing a part of a plurality of calcium ions in OCP.

As a result, a block material having the crystal of OCP in which a part of the plurality of calcium ions are replaced with the silver ions is obtained.

After the immersion, an excessive reaction solution is removed with distilled water, and the block material is completely dried, for example, in a dryer at 40° C.

In the block material of OCP in which the precursor ceramic block has been changed to a compact made of OCP in terms of the composition by being immersed in the solution, the outer form of the precursor ceramic block used is almost maintained.

Since the dimensions of the precursor ceramic block are almost taken over to the dimensions of the OCP-based block material having a composition converted to OCP with favorable reproducibility, it is possible to easily obtain a block material of OCP having predetermined dimensions without taking any changes in dimensions from the precursor into account.

The obtained block material of OCP is further subjected to phase conversion treatments S13A (hydrolysis or a hydrothermal reaction) and S23A (carbonation treatment), whereby it is possible to produce a block material of HAp, a block material of $CO_3Ap$ and the like.

When the phase of the obtained OCP-based block body is converted to a block body of Ap by ion replacement in a state of OCP, which is an unstable calcium phosphate than Ap, rather than direct ion replacement in a state of Ap, which is a stable calcium phosphate, it is possible to efficiently produce a block body having the crystal of Ap in which a part of a plurality of calcium ions have been replaced with silver ions or copper ions.

[Phase Conversion Process S13A]

In the phase conversion process S13A, the phase of the OCP-based block body is converted to a block body of HAp while maintaining the solid state by hydrolysis or a hydrothermal reaction in a phase conversion solution.

The phase conversion process S13A can be carried out in the same manner as the phase conversion process S3A except that the block body of OCP is used in place of the powder of OCP.

After the phase conversion, an excessive reaction solution is removed with distilled water, and the block material is completely dried, for example, in a dryer at 40° C.

[Phase Conversion Process S13B]

In the phase conversion process S13B, the phase of the block body of OCP is converted to a block body of $CO_3Ap$ while maintaining the solid state by a carbonation treatment in a phase conversion solution.

The phase conversion process S13B can be carried out in the same manner as the phase conversion process S3B except that the block body of OCP is used in place of the powder of OCP.

After the phase conversion, an excessive reaction solution is removed with distilled water, and the block material is completely dried, for example, in a dryer at 40° C.

In the block materials of replacement-type HAp and $CO_3Ap$ to be obtained, the outer form of the precursor ceramic block used is almost maintained.

Since the dimensions of the precursor ceramic block are almost taken over to the dimensions of the block material of Ap with favorable reproducibility, it is possible to easily obtain a block material of Ap having predetermined dimensions without taking any changes in dimensions from the precursor into account.

Ninth Embodiment

"Method for Producing Porous Material Having Replacement-Type Calcium Phosphate Crystal"

A ninth embodiment of the present invention is a method for producing a porous material in which a part of a plurality of calcium ions in the structure of the crystal of any one calcium phosphate selected from the group consisting of OCP, HAp, FAp, ClAp and $CO_3$Ap are replaced with silver ions or copper ions.

Figures 5, 6:
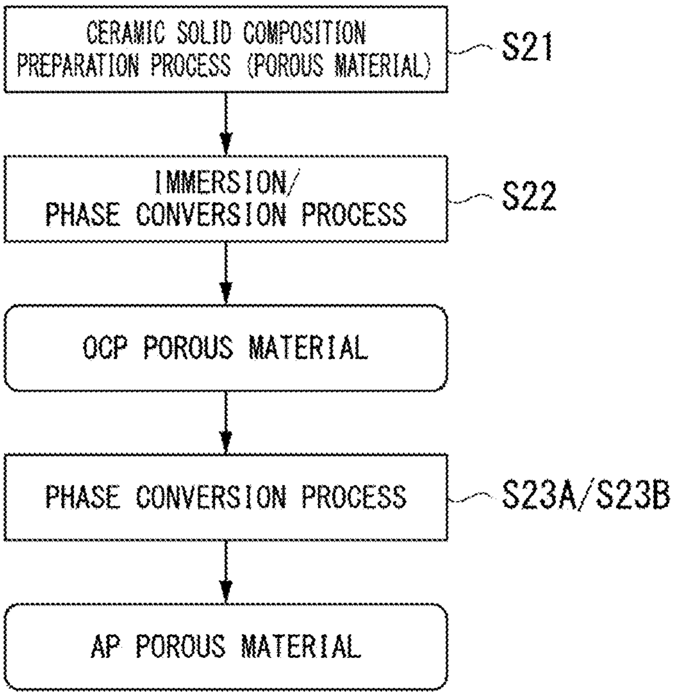
FIG. 5 is a flowchart showing process of a method for producing a porous material of a calcium phosphate according to a ninth embodiment of the present invention.
FIG. 6 is a table showing the numerical values of silver nitrate concentrations and the colors of powders of OCP supporting Ag.

FIG. 5 is a flowchart showing process of the method for producing a porous material of a calcium phosphate according to the ninth embodiment of the present invention.

The method for producing a porous material of the present embodiment includes a ceramic solid composition preparation process S21 of preparing a solid composition (porous material) made of ceramic containing at least one of calcium and phosphoric acid and a process S22 of immersing the solid composition in a solution containing the other of calcium and phosphoric acid and either or both of a silver ion or a complex ion of silver and a copper ion or a complex ion of copper and converting the solid composition to an octacalcium phosphate-based crystal to obtain a porous material, in which a part of a plurality of calcium ions in the structure of the octacalcium phosphate-based crystal are replaced with silver ions or copper ions.

In the method for producing a porous material of the present embodiment, for example, a solid composition made of ceramic containing at least one of calcium and phosphoric acid (porous precursor ceramic block) is immersed in a solution containing the other of calcium and phosphoric acid and either or both of a silver ion or a complex ion of silver and a copper ion or a complex ion of copper, and the solid composition is converted to a crystal of OCP.

The immersion/phase conversion process S22 in the present embodiment is the same process as the immersion/phase conversion process S12 in the eighth embodiment and thus will not be described in detail. A difference between the eight embodiment and the ninth embodiment is a difference in the ceramic solid composition that is subjected to the immersion/phase conversion process, and, the porous material is used in the present embodiment, but the block material is used in the eighth embodiment.

Hereinafter, a method for preparing the porous material that is used in the present embodiment will be described.

[Method for Preparing Porous Material (Porous Precursor Ceramic Block)]

First, the brushite cement powder, which has been described in the eighth embodiment, is used as a material and granulated. Next, pure water is blown to powder to granulated particles by spraying, thereby obtaining spherical brushite cement powder hardened spheres. Next, moisture is removed from the obtained brushite cement powder hardened spheres, and the brushite cement powder hardened spheres are classified into, for example, 0.10 to 0.25 mm, 0.25 to 0.50 mm, 0.50 to 1.00 mm and 1.00 to 2.00 mm.

Next, the classified brushite cement powder hardened spheres are packed into a mold, and an appropriate amount of a 0.1 mol/L to 1.0 mol/L monocalcium phosphate monohydrate-saturated $H_3PO_4$ solution is added dropwise. This initiates a hardening reaction by which the DCPD crystal is to be precipitated on the surfaces of hardened spheres. The brushite cement powder hardened spheres are hardened as they are while fixed with clips, whereby a porous material (porous precursor ceramic block) can be obtained.

The obtained porous material is subjected to the immersion/phase conversion process S22 as described above, whereby a porous material of OCP can be obtained.

The obtained porous material of OCP is subjected to the phase conversion process S23A, whereby a porous material of replacement-type HAp can be obtained. The phase conversion process S23A can be carried out in the same manner as the phase conversion process S3A except that the porous material of OCP is used in place of the powder of OCP.

The obtained porous material of OCP is subjected to the phase conversion process S23B, whereby a porous material of replacement-type $CO_3$Ap can be obtained. The phase conversion process S23B can be carried out in the same manner as the phase conversion process S3B except that the porous material of OCP is used in place of the powder of OCP.

Similar to the case of the block material, when the phase of the porous material of the obtained OCP is converted to an Ap-based porous material by ion replacement in a state of OCP, which is an unstable calcium phosphate than Ap, rather than direct ion replacement in a state of Ap, which is a stable calcium phosphate, it is possible to efficiently produce a porous material having the crystal of Ap in which a part of a plurality of calcium ions have been replaced with silver ions or copper ions.

Similar to the case of the eighth embodiment, in the porous material of OCP in which the porous precursor ceramic block has been changed to a compact made of OCP in terms of the composition, the outer form of the porous precursor ceramic block used is almost maintained.

Since the dimensions of the precursor are almost taken over to the dimensions of the porous material of OCP having a composition converted to OCP with favorable reproducibility, it is possible to easily obtain a porous material of OCP having predetermined dimensions without taking any changes in dimensions from the precursor into account.

In the eighth and ninth embodiments, the solution may contain a second composition containing cations excluding a silver ion, a copper ion and a calcium ion, and a part of a plurality of calcium ions in the structure of the crystal of OCP may be replaced with silver ions, copper ions and cations excluding these ions.

The second composition in the eighth and ninth embodiments is the same as the second composition in the seventh embodiment.

In the eighth and ninth embodiments, the solution may contain a second composition containing cations excluding a silver ion and a copper ion and a third composition containing anions excluding a phosphate ion and anions excluding a hydrogen phosphate ion, a part of a plurality of calcium ions in the structure of the crystal of OCP may be replaced with silver ions, copper ions and cations excluding these ions, and a plurality of phosphate ions or a plurality of hydrogen phosphate ions in the structure of the crystal OCP may be replaced with anions excluding a phosphate ion and anions excluding a hydrogen phosphate ion.

The third composition in the eighth and ninth embodiments is the same as the third composition in the seventh embodiment.

In addition, the concentrations of the silver ions or the copper ions in the solutions in the immersion/phase conversion process S12 and S22 may be in a range of 0.1 mmol/L to 200 mmol/L and preferably in a range of 2.5 mmol/L to 30 mmol/L.

EXAMPLES

Hereinafter, specific examples of the embodiments of the present invention will be described, but the present invention is not limited thereto.

Example 1

[Preparation of Powder of Ag-Containing OCP]

As powders having a crystal of OCP, powders of OCP containing Ag (hereinafter, referred to as "powders of Ag-containing OCP") were prepared by a method to be described below.

Diammonium hydrogen phosphate and silver nitrate were added to 20 ml of pure water such that the concentration of diammonium hydrogen phosphate reached 1.0 mol/L and the concentration of silver nitrate reached 0.000 mol/L, 0.001 mol/L, 0.005 mol/L, 0.010 mol/L, 0.030 mol/L, 0.050 mol/L and 0.100 mmol/L, respectively, and completely dissolved at 60° C. in an airtight container. Immediately after the dissolution reaction, yellow precipitation, which is considered to result from the generation of a salt of silver nitrate, occurred; however, as a result of continuously stirring the solutions at 60° C., in samples where the silver nitrate concentration was 0.000 mol/L, 0.001 mol/L, 0.005 mol/L, 0.010 mol/L or 0.030 mol/L, which were samples having a silver nitrate concentration of 0.030 mol/L or less, it was possible to obtain colorless and clear solutions.

Intrinsically, a Ag ion is precipitated as silver oxide or an insoluble salt such as silver phosphate under a weakly basic condition selected in the present examples. However, it is considered that, due to the action of a $NH_4$ ions as a coexisting ion, a complex ion of Ag and $NH_4$ was formed, which made it possible to obtain Ag solutions having a relatively high concentration while suppressing the occurrence of precipitation.

In a case where the samples containing more than 30 mmol/L silver nitrate were used for the preparation of the powders of OCP containing Ag, ammonium nitrate was further added to these solutions at a concentration of 2.0 mol/L. This made it possible to obtain colorless and clear solutions even at extremely high concentrations of silver nitrate of 0.050 mol/L and 0.1 mol/L.

Next, 2.39 g of calcium hydrogen phosphate dihydrate (DCPD) was added to the obtained solutions containing the complex ion, stirred for 10 minutes, then, left to stand at 60° C. and reacted for 24 hours. The obtained precipitates were separated from a liquid phase by the decantation method, then, washed with pure water and completely dried in a dryer set to 40° C. The obtained precipitates were white in the samples where the concentration of silver nitrate used in the reaction was 0.000 mol/L, 0.001 mol/L, 0.005 mol/L, 0.010 mol/L or 0.030 mol/L, which were the samples having a silver nitrate concentration of 0.03 mol/L or less, and were slightly yellow in the samples where the silver nitrate concentration was 50 mmol/L or 100 mmol/L, which exceeded the above-described concentrations.

The colors of the precipitates were measured from the dried precipitates as subjects by a reflection method using a color difference meter (manufactured by Nippon Denshoku Industries Co., Ltd., ZE-2000) according to the operation method annexed to the color difference meter. In addition, in order to evaluate metachromacy in biological environments, the precipitates were shaken in a phosphate buffered saline, and changes in the color shades of the precipitates were also evaluated by the same method.

The results are shown in FIG. 6. In FIG. 6, RGB values obtained by the measurement with the color difference meter and values obtained by converting these values to HSB values are shown together.

RGB is one of the color expression methods, three primary colors of red, green and blue are used as the basic elements, and specific colors are expressed by designating the brightness values thereof as integers of 0 to 255. The first one of the three values as the RGB value corresponds to the brightness of red, the second one corresponds to the brightness of green, and the third one corresponds to the brightness of blue.

HSB is a different color expression method from RGB and is composed of three components of hue, saturation and brightness. Colors expressed by RGB can be unambiguously converted to HSB values according to a certain calculation formula. The first value (hue) of the three values as the HSB value indicates the types of color with numerical values of 0 to 360 and expresses yellow at around 60, cyan at around 180 and magenta at around 300. The second value of the HSB value designates saturation as integers of 1 to 100, becomes low for achromatic colors and becomes high for bright colors. The third value of the HSB value indicates brightness, becomes higher as the color becomes close to white and becomes lower as the color becomes close to black.

In the samples where the silver nitrate concentration was 0.000 mol/L, 0.001 mol/L, 0.005 mol/L, 0.010 mol/L or 0.030 mol/L, which were the samples having a silver nitrate concentration of 0.03 mol/L or less, the degrees of coloration of the precipitates were low, and no noticeable changes in color after PBS shaking were observed. In the samples where the concentration of silver nitrate was 0.1 mol/L to 0.5 mol/L, precipitates appearing yellow before PBS shaking were confirmed, the colors significantly changed after the PBS shaking, and blue-red coloration was observed.

Figure 7:
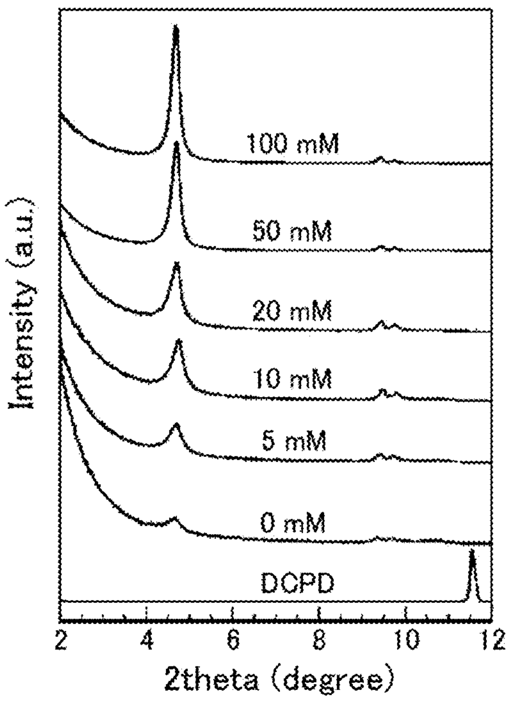
FIG. 7 is a graph showing XRD patterns of low-angle portions of powders of OCP supporting Ag.

Next, the obtained precipitates were identified by an X-ray powder structure analysis method. FIG. 7 is a graph showing XRD patterns of low-angle portions of powders of OCP supporting Ag. An appearance of the relative intensity of the characteristic peak of OCP at near 4.7 increasing with an increase in the silver nitrate concentration was confirmed, and it was found that the formation of the OCP crystal structure was derived. At the silver nitrate concentrations of 0.05 mol/L or more, peaks corresponding to silver phosphate ($Ag_3PO_4$) in addition to OCP were observed.

In order to evaluate the states of Ag being supported by the crystal of the precipitate identified as OCP by XRD, the states of functional groups in the precipitates were evaluated by an infrared spectroscopy (FT-IR: manufactured by Thermo Fisher Scientific, Nicolet NEXUS 670 FTIR).

In the unit lattices of OCP, there are 12 $PO_4$ groups, and six kinds of different chemical states are present. These $PO_4$ groups are in conjugate relationships with Ca ions or OH groups that are all different from one another, and a change in the state or kind of the ion in a conjugate relationship also accordingly changes the chemical state of the $PO_4$ group.

Therefore, it is possible to presume the kind of a cation that is conjugated with the $PO_4$ group by detecting a change in the chemical state of the $PO_4$ group.

Figure 8:
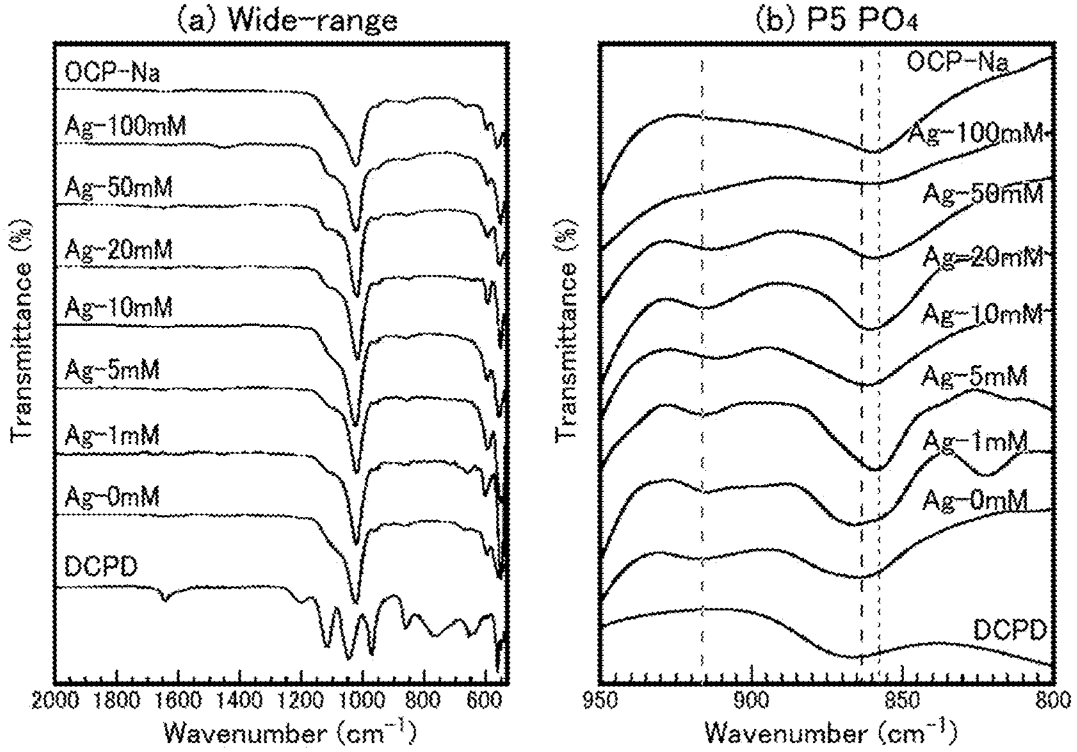
FIG. 8 is a graph showing FT-IR spectra of the powders of OCP supporting Ag. Dotted lines drawn in the vertical direction are auxiliary lines for comparison, the two auxiliary lines drawn at 916 $cm^{-1}$ and 864 $cm^{-1}$ show wave numbers at which a band is detected in samples containing no alkali metal, and one dotted line drawn at 857 $cm^{-1}$ shows wave numbers of bands detected in a case where a silver ion-containing solution containing no powder of OCP is used as a sample.

FIG. 8 is a graph showing FT-IR spectra of the powders of OCP supporting Ag.

As the silver nitrate concentration increased, the chemical state of the $PO_4$ group that was positioned at the base of a $HPO_4$—OH layer structure, which is called P5 $PO_4$, further changed (FIG. 8). From this fact, it was found that Ag is supported in the crystal structure of OCP in a manner of partially replacing Ca ions in a conjugate relationship with P5 $PO_4$, which is present at the base of the $HPO_4$—OH layer structure.

Furthermore, how much Ag is supported in the crystal structure of OCP was evaluated. The obtained precipitates were completely dissolved in 2% nitric acid, the concentrations of Ca, $PO_4$ and Ag in the solutions were measured by inductively coupled plasma atomic emission spectroscopy (ICP-AES: manufactured by Agilent Technologies Japan, Ltd., 5110 VDV), and the proportions were obtained, thereby measuring how much Ag was supported in the crystal structure of OCP.

Figure 9:
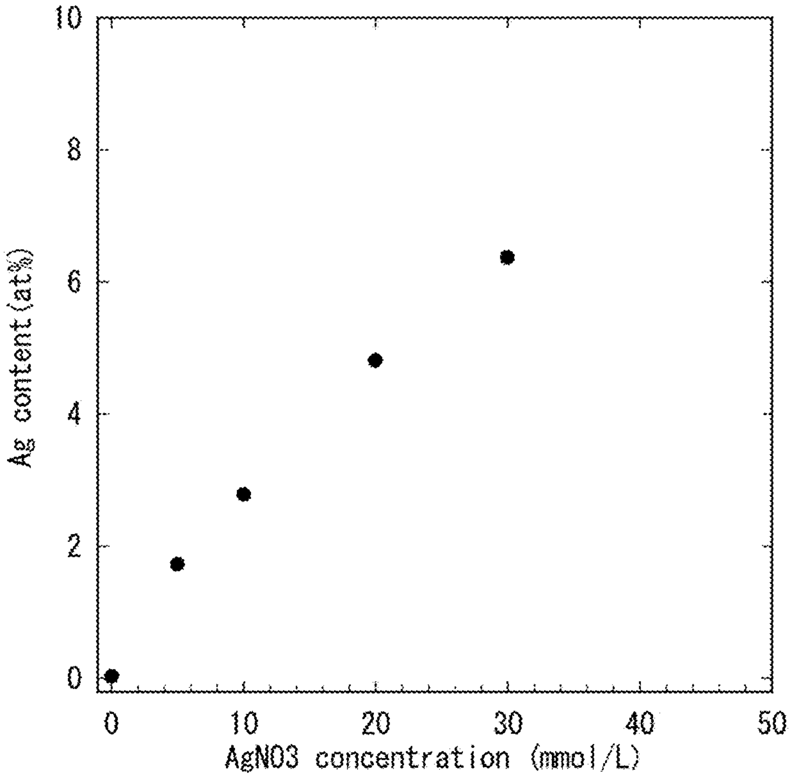
FIG. 9 is a graph showing a relationship between a concentration of a silver nitrate solution and a silver concentration in a powder of OCP during a treatment of a powder of Ag-substituted OCP.

FIG. 9 is a graph showing a relationship between the concentration of a silver nitrate solution and the silver concentration in the powder of OCP during a treatment of the powder of Ag-substituted OCP. As shown in FIG. 9, it was found that Ag was contained in the precipitates even in the precipitates synthesized at silver nitrate concentrations at which a silver compound such as silver phosphate was not detected. It was found that a maximum of approximately 6.4 at % of Ag is supported in OCP.

From the measurement results by ICP-AES, the chemical composition of OCP supporting Ag (hereinafter, referred to as "Ag-substituted OCP") can be estimated. It was confirmed that the chemical compositions of Ag-substituted OCP prepared in the present examples satisfied $Ca_{8-a}Ag_b(PO_4)_4(HPO_4)_{2+c}\cdot 5H_2O$ ($a \leq 2$ and $b \leq 2$).

Example 2

[Preparation of Powder of Cu-Containing OCP]

Powders of Cu-containing OCP were prepared by the same method as in Example 1 using copper nitrate trihydrate in place of silver nitrate used for the preparation of complex ion solutions.

A plurality of samples in which the concentration of copper nitrate trihydrate was in a range of 0 to 0.2 mol/L were prepared. In a solution containing 0.2 mol/L copper nitrate, a blue gel-form precipitate was observed. At concentrations of lower than 0.2 mol/L, the solutions appeared ultramarine.

2.39 g of DCPD was added to 20 ml of a complex ion solution and then reacted at 60° C. for 24 hours, and the obtained solid-phase powder (precipitate) was separated by the decantation method and washed with distilled water a plurality of times.

The washed solid-phase powder was completely dried at 40° C. to be made into a powder sample.

The obtained powder samples were analyzed and evaluated by XRD, ICP-AES and FT-IR in the same manner as in Example 1.

In all solutions having a copper ion, peaks at 4.7° that correspond to the (100) diffraction peak of OCP were observed. In addition, as a result of obtaining the ratios between the peak intensity at 4.7° and the peak intensity at 9.2°, which is multiple diffraction, the peak intensity ratio increased compared with those of systems where no copper ions were contained. This fact suggested that Cu is supported in the P5 $PO_4$ conjugate side of OCP.

In the analysis by ICP-AES, it was shown that, as the concentration of copper nitrate in the reaction solution increased, the concentration of Cu in the sample also linearly increased.

From FT-IR spectra, an appearance of the chemical state of P5 $PO_4$ further fluctuating with an increase in the Cu ion concentration in the solution was observed, and it was suggested that Cu was supported in this position.

From the above-described facts, it was shown that copper ions are also, similar to silver ions, supported by an OCP crystal in a manner of replacing a part of a plurality of calcium ion of the OCP crystal.

Example 3

"Preparation of Powders of Ag-Containing HAp and $CO_3$Ap"

As powders having a crystal of HAp, powders of HAp containing Ag (hereinafter, referred to as "powders of Ag-containing HAp") were prepared by a method to be described below. At the same time, as powders having a crystal of $CO_3$Ap, powders of $CO_3$Ap containing Ag (hereinafter, referred to as "powders of Ag-containing $CO_3$Ap") were prepared by a method to be described below.

0.4 g of a powder of Ag-containing OCP (concentration of silver nitrate: 0.02 mol/L) prepared by the method described in Example 1 was immersed in each of 20 ml of distilled water and $(NH_4)_2CO_3$ solutions having different concentrations (0.1 mol/L, 0.2 mol/L, 0.5 mol/L, 1.0 mol/L and 2.0 mol/L) at 80° C. for three days.

After the immersion, solid-phase components were washed with distilled water several times and dried in a dry oven at 80° C. for one day, thereby obtaining powders of Ag-containing HAp and $CO_3$Ap.

The obtained powders of Ag-containing HAp and $CO_3$Ap were analyzed by the same method as in Examples 1 and 2.

Figure 10:
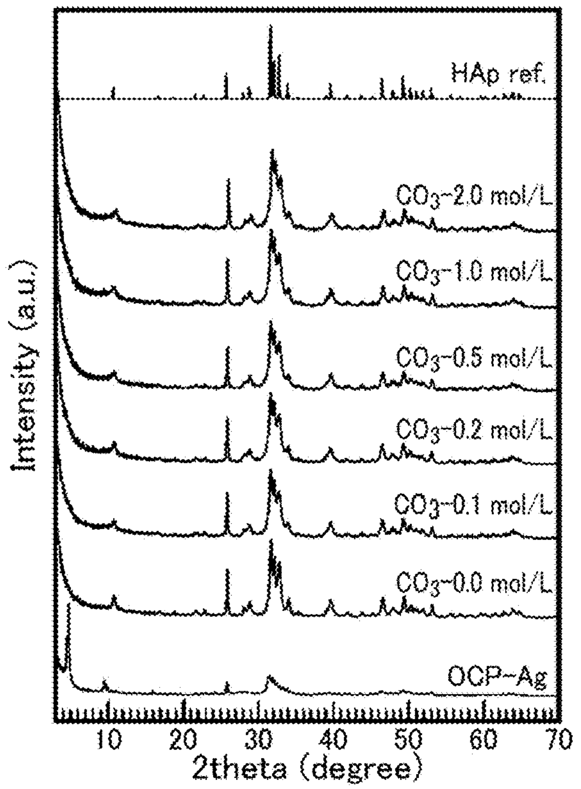
FIG. 10 is a graph showing XRD patterns of powders of OCP supporting Ag, HAp and $CO_3Ap$.

FIG. 10 is a graph showing XRD patterns. In all samples, the characteristic peaks of OCP at near 4.7° disappeared, and XRD patterns analogous to that of an HAp specimen for reference were shown.

In addition, as a result of observing the obtained samples with SEM, no significant changes in the microscopic form of the powder were recognized (observation photographs are not shown).

As a result of analyzing the introduction of $CO_3$ ions into the crystal lattices from changes in d-spacings and IR analysis regarding the obtained samples, the introduction of $CO_3$ ions into the crystal lattices was recognized in samples for which the $(NH_4)_2CO_3$ solution was used for immersion (the results of the changes in the d-spacings are not shown).

Figure 11:
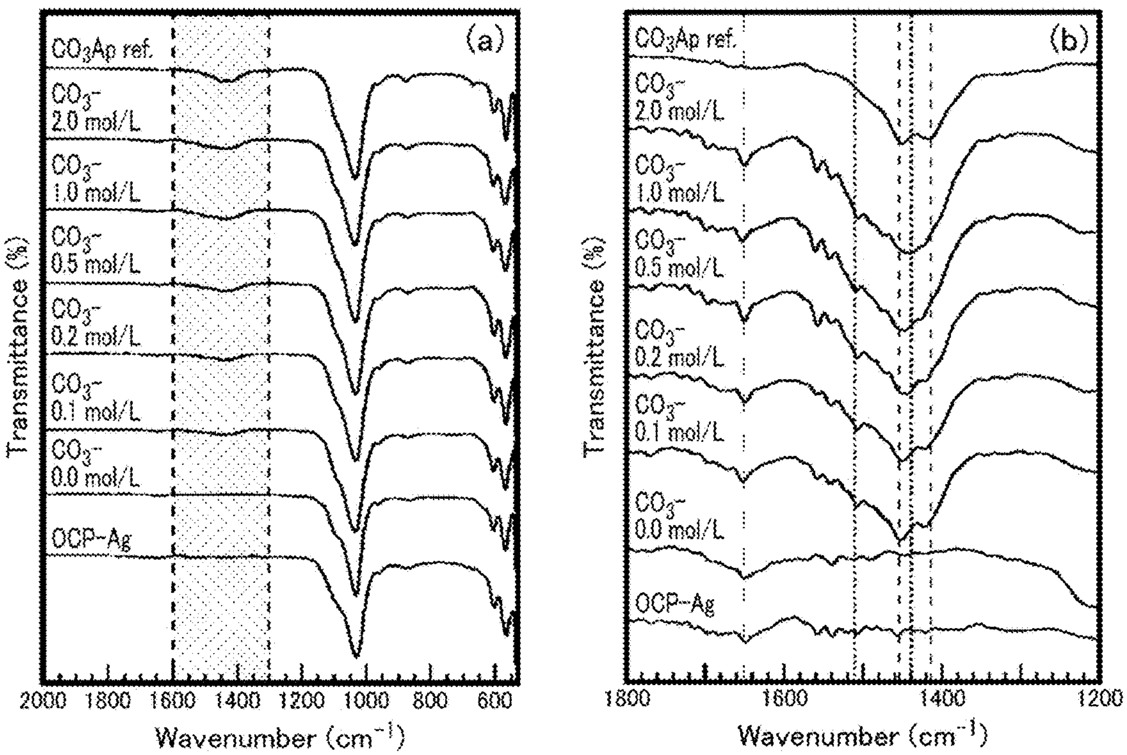
FIG. 11 is a graph showing FT-IR spectra of the powders of OCP supporting Ag, HAp and $CO_3Ap$.

FIG. 11 is a graph showing the FT-IR spectra of HAp and $CO_3$Ap powders supporting Ag.

In the samples for which the $(NH_4)_2CO_3$ solution was used for immersion, the absorption bands of $CO_3$ were recognized at near 1400 to 1500 $cm^{-1}$. On the other hand, in samples for which the powder was immersed in distilled water and subjected to a phase conversion treatment ($CO_3$—0.0 mol/L), no absorption bands of $CO_3$ were recognized.

Figure 12:
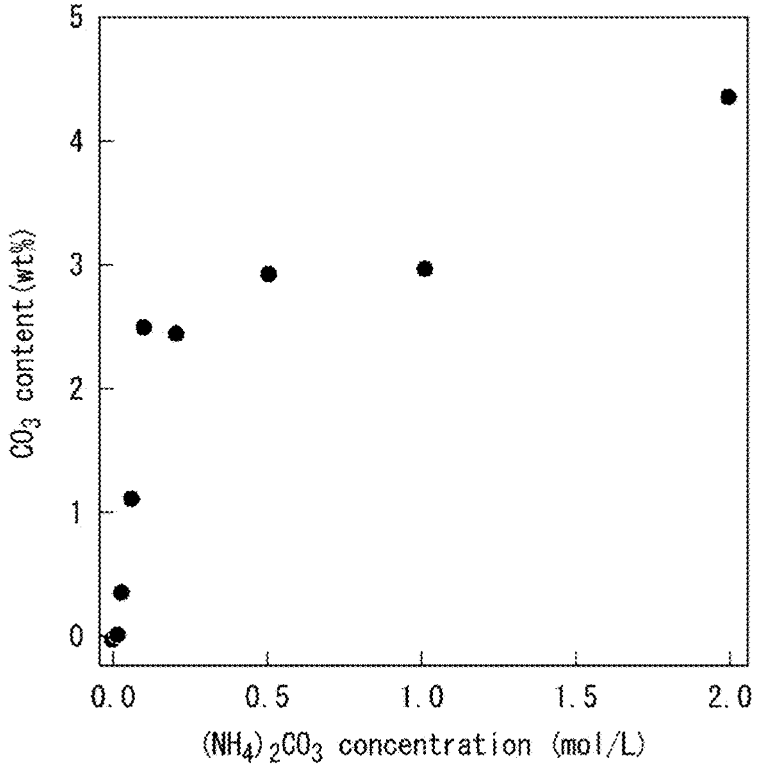
FIG. 12 is a graph showing a relationship between a concentration of an ammonium carbonate solution and a Ag concentration in powders of Ag-substituted HAp and $CO_3Ap$ during a treatment of the powders of the HAp and $CO_3Ap$.

FIG. 12 is a graph showing the measurement results of the content of COs in the powder samples by thermal analysis. As a result of analyzing the obtained samples by thermal analysis, it was shown that, as the concentration of the $(NH_4)_2CO_3$ solution becomes higher, the content of $CO_3$ contained increases.

Next, how much Ag was held in HAp or $CO_3$Ap, the phase of which had been converted from Ag-containing OCP, was investigated.

Figure 13:
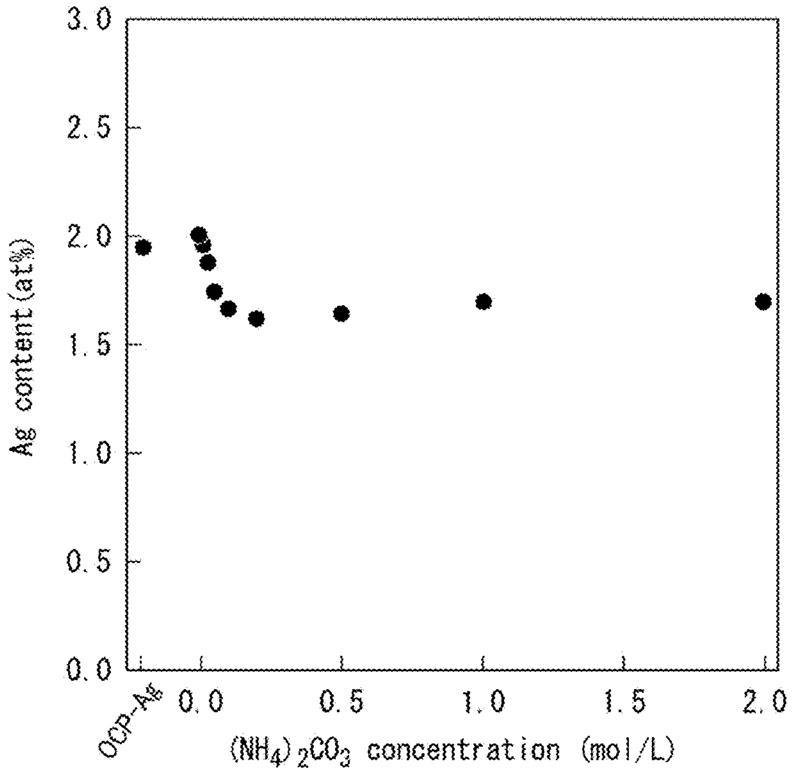
FIG. 13 is a graph showing a relationship between a concentration of a silver nitrate solution and a silver concentration in a powder of OCP during a treatment of powders of Ag-substituted HAp and $CO_3Ap$.

FIG. 13 is a graph showing the relationship between the contents of Ag in the obtained samples and the $(NH_4)_2CO_3$ solution concentrations during immersion.

In the sample where the powder was subjected to phase conversion in a state of being immersed in distilled water, the same level (2.0 atom %) of Ag as in Ag-containing OCP, which was the starting material, was contained. In the samples where the $(NH_4)_2CO_3$ solution of a low concentration was used as well, the same level of Ag as in Ag-containing OCP was contained. In the samples where the 0.1 mol/L to 2.0 mol/L $(NH_4)_2CO_3$ solution was used, the Ag content decreased slightly (1.6 atom %); however, when the concentration was in a range of 0.2 mol/L or more, a concentration-dependent decrease in the Ag content rate was not shown, and almost constant values were retained.

Example 4

[Preparation of Powder of Ag-Substituted OCP with More Developed OCP Structure]

In the powders of Ag-substituted OCP prepared in Example 1 (hereinafter, referred to as "powders of Ag-substituted OCP"), since Ag was partially in a conjugate relationship with the P5 $PO_4$ group in the OCP crystal structure, the development of the $HPO_4$—OH layer structure, which is an intrinsic structure of OCP, was partial. Therefore, attempts were made to prepare powders of Ag-substituted OCP for which the OCP structure was further developed by further supporting Na ions.

Sodium nitrate was further added to a solution containing 1.0 mol/L diammonium hydrogen phosphate and 0.0 to 0.1 mol/L silver nitrate such that the concentration reached 0.0 to 1.0 mol/L, and the development of the interlayer structure of OCP crystal and the properties of supporting Ag and Na being supported by OCP were evaluated.

Figure 14:
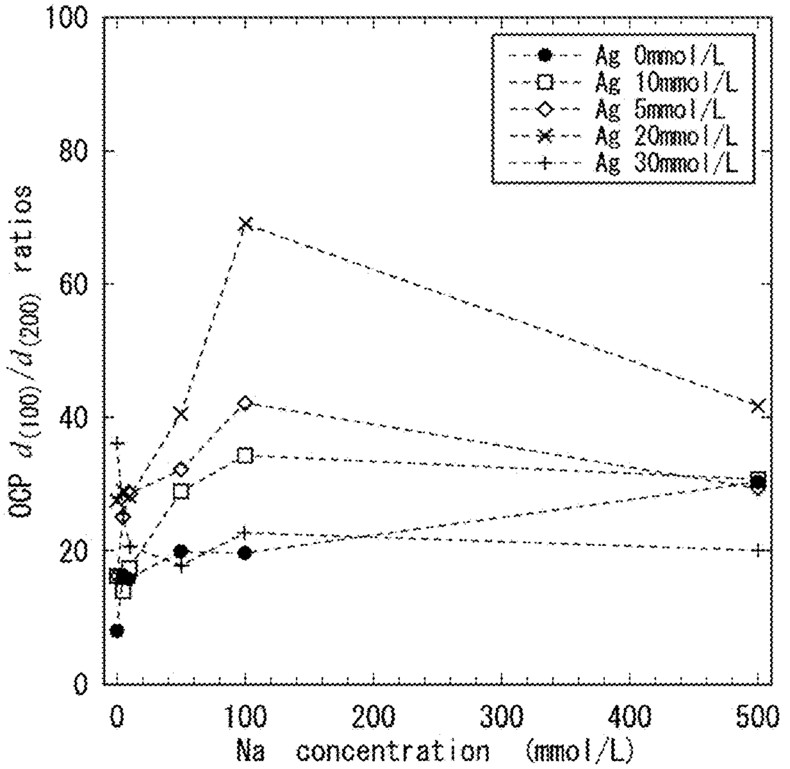
FIG. 14 is a graph showing a relationship between the sum of concentrations of silver nitrate and sodium nitrate and development of an OCP layer structure.

FIG. 14 is a graph showing the relationship between the sum of the concentrations of silver nitrate and sodium nitrate and the development of the OCP layer structure.

It was found by analysis by XRD that, when the sum of the concentrations of silver nitrate and sodium nitrate was 0.1 mol/L or more, cations thereof improved the conjugate relationship with the P5 $PO_4$ group, whereby the OCP layer structure extremely developed (FIG. 14).

Next, the amount of Ag supported in the crystal powder of OCP by the containing of Na was evaluated. Since Na and Ag am supported by sites present at two isotopes in the crystal structure of OCP, it is suggested that the amount of Ag supported fluctuates by a mechanism such as competition or conjugation. Therefore, the influence of Na on the amount of Ag supported was studied by analyzing elements using ICP-AES for the obtained OCP samples.

Figure 15:
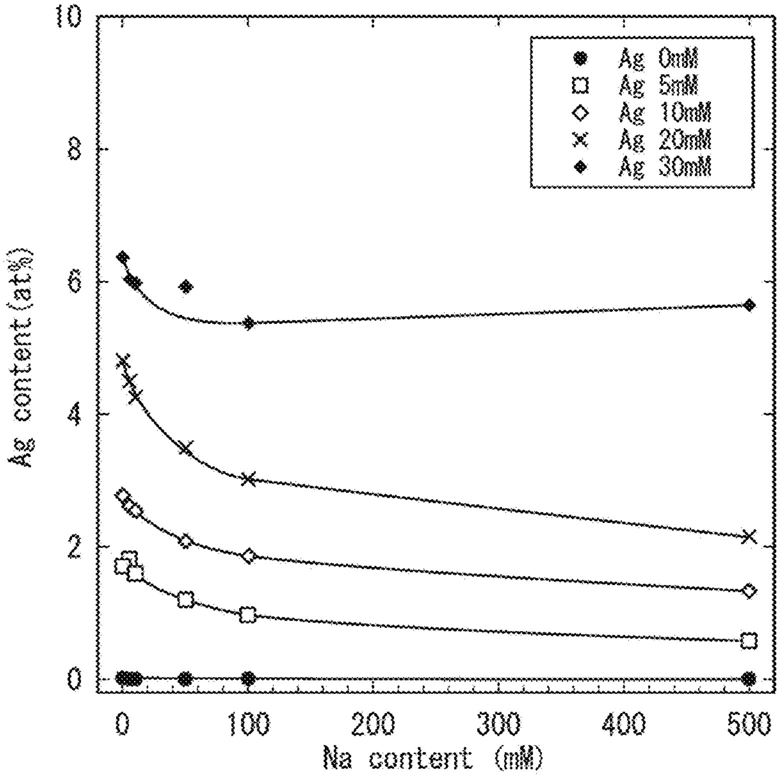
FIG. 15 is a graph showing a relationship between a Na concentration and a Ag concentration in powders of OCP.

FIG. 15 is a graph showing the relationship between the Na concentration and the Ag concentration in the powders of OCP. While also depending on the concentration of the silver nitrate solution used during synthesis, the Ag concentration in OCP gradually decreased as the concentration of sodium nitrate increased. Compared with a system not containing sodium nitrate, the amount of Ag supported in OCP decreased by approximately 30% to 80% in a system with 0.5 mol/L sodium nitrate (FIG. 15). However, as shown in Example 5 to be described below, even after the amount of Ag supported gradually decreases, a sufficient antibacterial property is exhibited. It was confirmed that the chemical compositions of the samples satisfied $Ca_{8-a}Na_bAg_c(PO_4)_4(HPO_4)_{2+d}\cdot 5H_2O$ (b+c≤2).

Example 5

[Preparation of Ag-Substituted OCP-Based Block Material]

50 g of calcium carbonate, 172 g of calcium hydrogen phosphate dihydrate and 30 mL of a 1% polyvinyl alcohol-1% polyethylene glycol solution were put into a zirconia jaw of a planetary ball mill together with zirconia balls and crushed with a planetary ball mill (P-5) manufactured by Fritsch GmbH at 200 rpm for one hour, and these were completely mixed.

After that, the mixture was put into an alumina plate and fired at 900° C. for 12 hours in an electric furnace, thereby obtaining β-tricalcium phosphate (β-TCP, $Ca_3(PO_4)_2$). The obtained sample was identified by XRD. 5 g of the obtained β-TCP and 3 g of monocalcium phosphate monohydrate (MCPM: $Ca(H_2PO_4)_2\cdot H_2O$ were mixed in a well-dried mortar for 30 minutes, thereby obtaining a brushite cement powder. In order to prevent deterioration by moisture absorption, the obtained brushite cement powder was stored at 60° C.

Approximately 0.1 g of the brushite cement powder was packed into a silicon rubber sheet mold (46×3 mm), then, 0.02 mL of 70% ethanol was added dropwise, and the brushite cement powder was compressed with clips, thereby primarily hardening a powder mixture. After the primary hardening, the powder mixture was cured at a humidity of 100% and 40° C. for 24 hours or longer while being compressed, thereby completing the primary hardening. After that, the clips were removed, and the powder mixture was exposed to water vapor again at a humidity of 100% and 40° C. for 24 hours or longer, thereby obtaining a DCPA hardened body, which was to serve as a precursor ceramic block.

10 DCPA hardened bodies obtained were immersed in a 20 mL of a solution containing 1 mol/L ammonium hydrogen phosphate, 0.02 mol/L silver nitrate and 2 mol/L sodium nitrate at 70° C. for three days. After the immersion, an excessive reaction solution was removed with distilled water, and the DCPA hardened bodies were completely dried in a dryer at 40° C.

Figure 16:
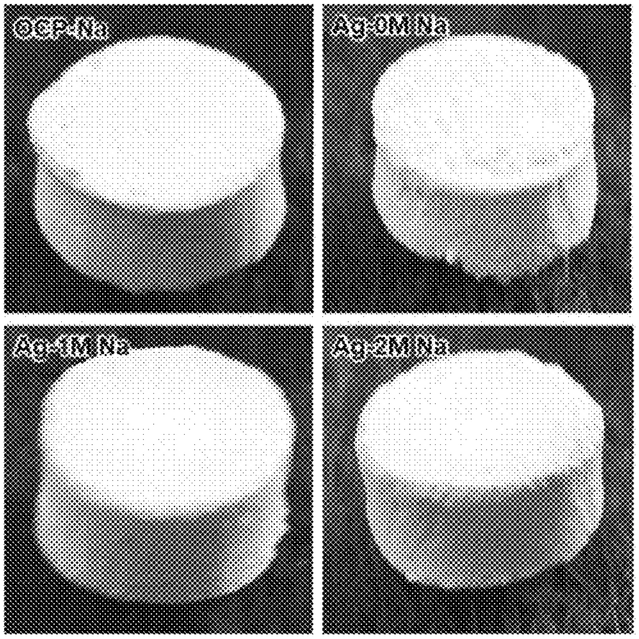
FIG. 16 is photographs of Ag-substituted OCP-based block materials.

FIG. 16 shows photographs of Ag-substituted OCP-based block materials. The immersed compacts almost maintained the outer forms of the DCPA hardened bodies, which were precursor ceramic blocks (FIG. 16). The diametral tensile strengths were measured at a crosshead speed of 1 mm/m with a universal tester (AGS-X) manufactured by Shimadzu Corporation and found out to be 2.5±0.8 MPa.

Figure 17:
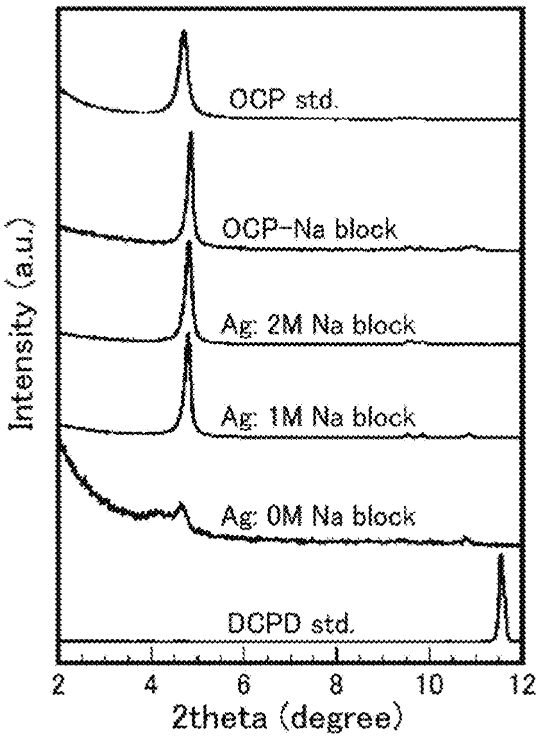
FIG. 17 is a graph showing XRD patterns of the Ag-substituted OCP-based block material.

The XRD patterns of the block materials of Ag-substituted OCP are shown. As a result of XRD measurement of test pieces, it was found that the compositions were converted to compacts almost composed of OCP (FIG. 17).

The phases of the obtained block materials of OCP were converted in a solid state, whereby, similar to the case of OCP, it was possible to produce block materials of HAp and $CO_3$Ap (the data are not shown).

Example 6

[Preparation of Porous Material of Ag-Substituted OCP]

Approximately 1 g of each of the brushite cement powders prepared in Example 3 was put into a pan-type granulator, the pan was inclined 40° and rotated at a rotation rate of 20 rpm to adjust the brushite cement powder so as to slide down in the pan-type granulator.

Pure water was blown thereto using a sprayer to harden the powder in a spherical shape, thereby obtaining a spherical brushite cement powder hardened body. The granulator was held in a state of being rotated for 30 minutes or longer to remove surplus water, and then a reaction product made of the obtained brushite cement powder hardened body was put on a polystyrene tray and dried at 40° C. After that, the brushite cement powder hardened spheres were classified into 0.10 to 0.25 mm, 0.25 to 0.50 mm, 0.50 to 1.00 mm and 1.00 to 2.00 mm using a sieve shaker. The classified brushite cement powder hardened spheres were stored at 60° C.

The classified brushite cement powder hardened spheres were packed into a silicon rubber sheet mold (46×3 mm), then, 0.02 mL of a 0.4 to 0.9 mol/L calcium dihydrogen phosphate-saturated $H_3PO_4$ solution was added dropwise, and then a hardening reaction by which a DCPD crystal was to be precipitated on the surfaces of the hardened spheres was initiated with the brushite cement powder hardened spheres fixed with clips, thereby obtaining a pellet-shaped compact having a porous structure therein.

10 pellet-shaped compacts obtained were immersed in a 20 mL of a solution mixture of 1 mol/L ammonium hydrogen phosphate-0.02 mol/L silver nitrate and 2 mol/L sodium nitrate at 70° C. for three days. After the immersion, an excessive reaction solution was removed with distilled water, and the DCPA hardened bodies were completely dried in a dryer at 40° C.

Figure 18:
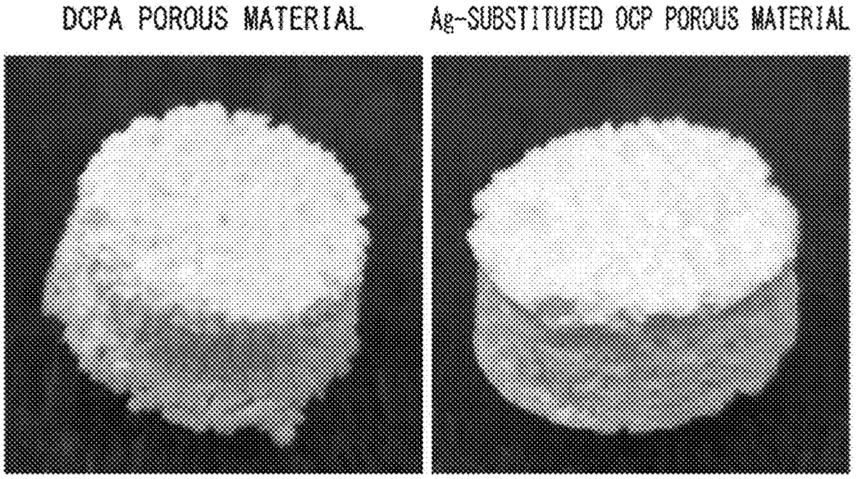
FIG. 18 is a photograph of a Ag-substituted OCP-based porous material.

The immersed pellet-shaped compacts almost maintained the outer forms of the DCPA hardened bodies, which were precursor ceramic blocks (FIG. 18).

Figure 19:
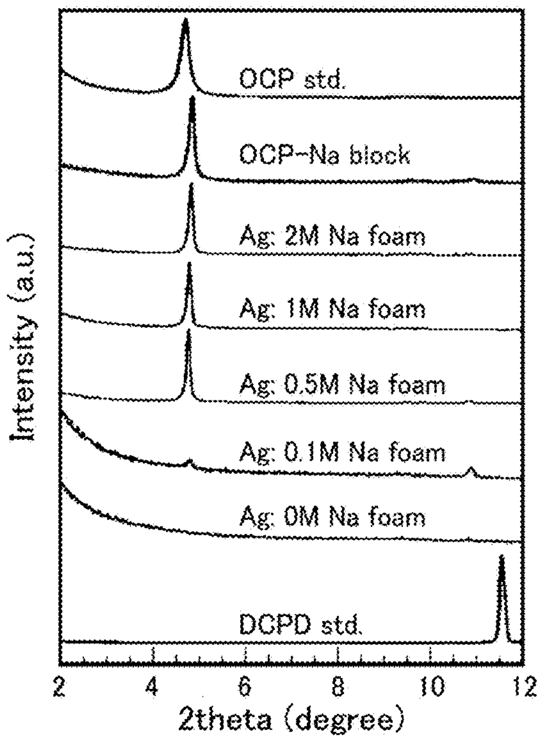
FIG. 19 is a graph showing XRD patterns of the Ag-substituted OCP-based porous material.

The diametral tensile strengths were measured at a cross-head speed of 1 mm/m with a universal tester (AGS-X) manufactured by Shimadzu Corporation and found out to be 0.36 MPa. In addition, as a result of XRD measurement of test pieces, it was found that the compositions were converted to compacts almost composed of OCP (FIG. 19).

The phases of the obtained porous bodies of OCP were converted in a solid state, whereby, similar to the case of OCP, it was possible to produce porous bodies of HAp and $CO_3Ap$ (the data are not shown).

Example 7

[Evaluation of Antibacterial Property of Powder of Ag-Substituted OCP Against *S. mutans*]

The minimal growth inhibitory concentration of the powder of Ag-substituted OCP to *Streptococcus mutans* (*S. mutans*) was evaluated. *S. mutans* of a type culture strain (*Streptococcus mutans* Clark 1924, ATCC 25175) was inoculated into a heart infusion broth medium (Eiken Chemical Co., Ltd., Product No.: E-MC04 110929). The *S. mutans* was shaken and cultured in 5 mL of the broth medium put into an L-like tube at 37° C. for 24 hours at a shaking rate of 100 rpm.

After the fact that the *S. mutans* was in a logarithmic growth phase was confirmed by measuring the absorbance at 630 nm using an absorption spectrometer, 0.1 mL of a fungus liquid was taken and newly inoculated into 5 mL of the broth medium.

The powder of Ag-substituted OCP prepared in Example 1 was suspended therein such that the concentration thereof reached 0.01 g/mL. The powder was made to act at 37° C. for 24 hours at a shaking rate of 100 rpm, and the antibacterial property of the powder of Ag-substituted OCP was evaluated.

After the 24-hour action, the powder was left to stand for five minutes in a room-temperature environment, the powder of Ag-substituted OCP suspended in the broth medium was precipitated, then, the supernatant was appropriately diluted with a PBS solution, and then 0.1 mL of the powder was inoculated into an agar medium (ϕ100). After the powder was cured at 37° C. for three days, the number of colonies formed on the agar medium was counted, and the antibacterial property was evaluated.

In addition, in order to evaluate the growing property of the *S. mutans* on the powder of Ag-substituted OCP after the action, the Ag-substituted OCP powder after the action was washed with PBS a plurality of times, then, fixed with neutral buffered formalin, dehydrated and observed with a scanning electron microscope (SEM).

Furthermore, in order to measure the concentration of Ag eluted into the medium, the medium was filtered with a 200 nm syringe filter and then diluted 20 times with 2% nitric acid, and the concentration of Ag ions in the solution was measured by ICP-AES.

Figure 20:
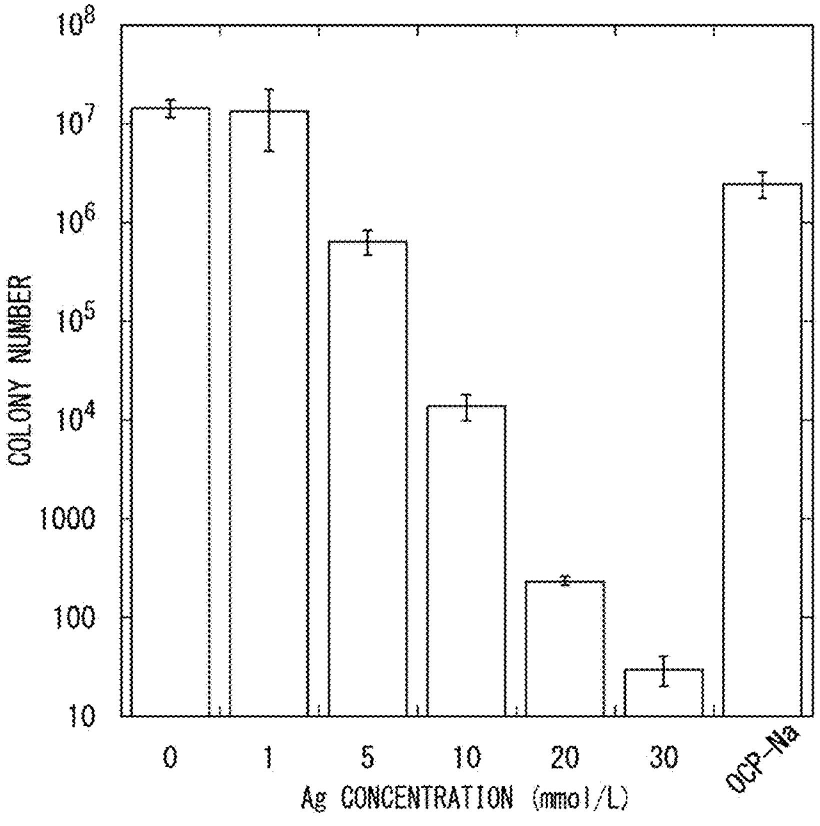
FIG. 20 is a graph showing a concentration of silver nitrate used at the time of preparing a Ag-substituted OSP-based block material and an antibacterial activity of the prepared OSP-based powder.
Figure 21:
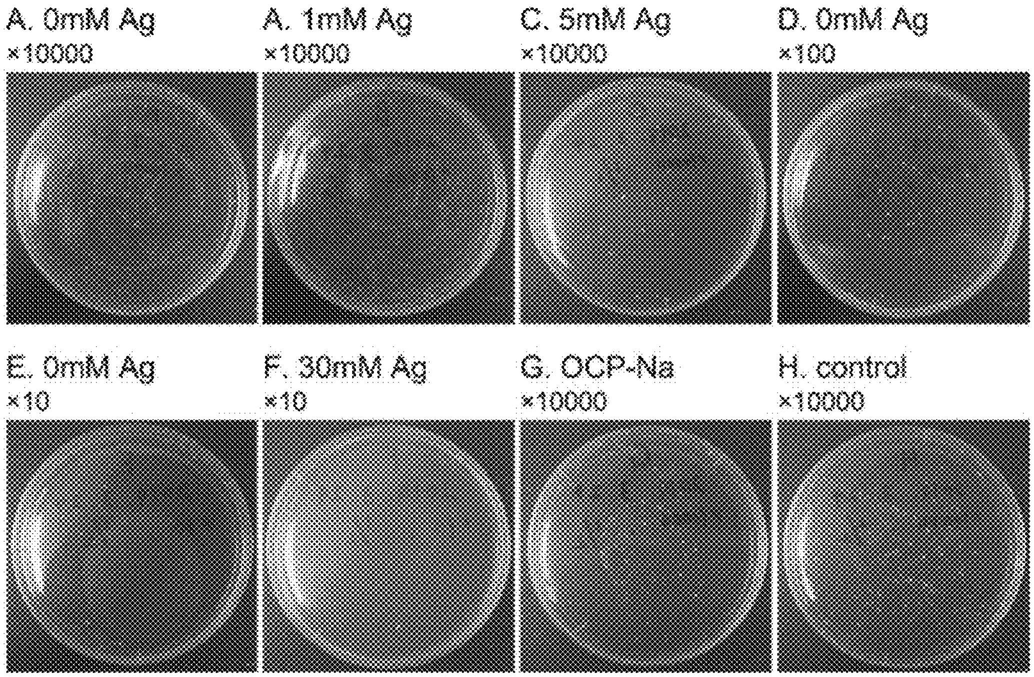
FIG. 21 is photographs showing states where agar media are smeared with *S. mutans* culture fluids on which a Ag-substituted OSP-based powder has been caused to act and then colonies are formed.

In the powder of OCP where the Ag concentration in the powder of Ag-substituted OCP was 1.5 at % or more, the number of colonies formed significantly decreased (FIG. 20). At an Ag concentration of 2.7 at % or more, it was found that, compared with that in OCP not supporting Ag, the number of colonies was approximately 1/100 and the antibacterial effect was significant (FIG. 21).

Figure 22:
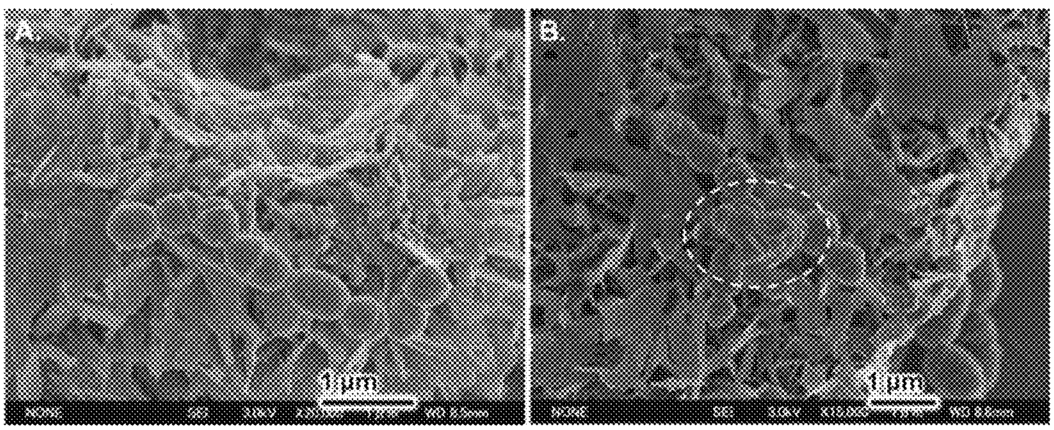
FIG. 22 is electron micrographs showing the observation of *S. mutans* attached onto Ag-substituted OCP powders.

In addition, as a result of visually observing fungi on the powder, a structure in which spherical fungi were connected in a row was observed at a Ag concentration of 1.5 at % or less, and, in a sample with an Ag concentration of 2.7 at %, only an extremely small number of fungi were observed, and furthermore, collapse of some of fungi themselves was observed (FIG. 22).

In addition, at concentrations of 2.7 at % or more, it was not possible to observe fungi themselves.

In addition, from the medium after the action, as Ag, almost the detection limit or less of Ag ions alone were measured. Therefore, it is considered that Ag does not exert an antibacterial property by being dissolved in a medium, but exhibits an antibacterial property by being brought into contact with a medium.

Comparative Example 1

[Preparation of Ag-Substituted OCP Powder in Solution not Containing $NH_4$]

In order to evaluate the dispersion power of $NH_4$ ions in a basic solution of Ag ions, $Na_2HPO_4$ was used as a basic phosphoric acid solution in place of a $(NH_4)_2HPO_4$ solution.

Disodium hydrogen phosphate and silver nitrate were added to 20 ml of pure water such that the concentrations thereof reached 1.0 mol/L and 0.0 to 0.1 mol/L, respectively, and stirred in an airtight container at 60° C. As a result, when the concentration of a silver nitrate solution was 0.001 mol/L or more, an appearance in which yellow precipitates generated in the solution were not dissolved, but suspended was observed.

As a result of attempting to prepare OCP by hydrolyzing DCPD in a suspension where these yellow precipitates were generated, precipitates significantly colored to yellow were obtained. All of the obtained precipitates contained silver phosphate.

INDUSTRIAL APPLICABILITY

It is possible to provide a bone substitute material or the like that is more useful than ever.

The invention claimed is:

1. A crystal of a calcium phosphate that is octacalcium phosphate, wherein a part of a plurality of calcium ions in a crystal structure of the crystal are replaced with a silver ion or a copper ion.

2. The crystal of a calcium phosphate according to claim 1, wherein a content rate of a silver atom or a copper atom is 0.01 atom % or more and 13.00 atom % or less.

3. The crystal of a calcium phosphate according to claim 1, wherein a content rate of a silver atom or a copper atom is 0.10 atom % or more and 10.00 atom % or less.

4. The crystal of a calcium phosphate according to claim 1, wherein a content rate of a silver atom or a copper atom is 1.00 atom % or more and 7.00 atom % or less.

5. The crystal of a calcium phosphate according to claim 1, wherein a content rate of a silver atom or a copper atom is 2.00 atom % or more and 5.00 atom % or less.

6. A powder comprising:

the crystal of a calcium phosphate according to claim 1.

7. A block material comprising:

the crystal of a calcium phosphate according to claim 1.

8. A porous material comprising:

the crystal of a calcium phosphate according to claim 1.

9. A bone substitute material comprising:

the crystal of a calcium phosphate according to claim 1.

10. An oral bone substitute material comprising:

the crystal of a calcium phosphate according to claim 1.

11. A method for producing a crystal of a calcium phosphate that is octacalcium phosphate, comprising:

a process of dissolving a silver-containing composition or a copper-containing composition in a solvent containing water to prepare a solution containing a complex ion of a silver ion or a copper ion; and a process of adding a compound containing phosphoric acid, hydrogen and calcium to the solution to form a crystal of octacalcium phosphate, wherein a part of a plurality of calcium ions in a structure of the crystal of the calcium phosphate are replaced with a silver ion or a copper ion.

12. The method for producing a crystal of a calcium phosphate according to claim 11, wherein a concentration of the silver ion or the copper ion in the solution in the process of preparing the solution in a range of 0.1 mmol/L to 200 mmol/L.

13. The method for producing a crystal of a calcium phosphate according to claim 11, wherein a concentration of the silver ion or the copper ion in the solution in the process of preparing the solution is in a range of 2.5 mmol/L to 30 mmol/L.

14. A method for producing a block material containing a crystal of a calcium phosphate that is octacalcium phosphate, comprising:

a process of immersing a solid composition made of ceramic containing at least one of calcium and phosphoric acid in a solution containing the other of calcium and phosphoric acid and a silver ion, a complex ion of silver, a copper ion or a complex ion of copper and converting some of the solid composition to a crystal of octacalcium phosphate to obtain the block material, wherein a part of a plurality of calcium ions in a structure of the crystal of the octacalcium phosphate are replaced with a silver ion or a copper ion.

15. The method for producing a block material according to claim 14, wherein a concentration of the silver ion or the copper ion in the solution is in a range of 0.1 mmol/L to 200 mmol/L.

16. The method for producing a block material according to claim 14, wherein a concentration of the silver ion or the copper ion in the solution is in a range of 2.5 mmol/L to 30 mmol/L.

17. A method for producing a porous material containing a crystal of a calcium phosphate that is octacalcium phosphate, comprising:

a process of immersing a solid composition made of ceramic containing at least one of calcium and phosphoric acid in a solution containing the other of calcium and phosphoric acid and a silver ion, a complex ion of silver, a copper ion or a complex ion of copper and converting some of the solid composition to a crystal of octacalcium phosphate to obtain the porous material, wherein a part of a plurality of calcium ions in a structure of the crystal of the octacalcium phosphate are replaced with a silver ion or a copper ion.

18. The method for producing a porous material according to claim 17, wherein a concentration of the silver ion or the copper ion in the solution is in a range of 0.1 mmol/L to 200 mmol/L.

19. The method for producing a porous material according to claim 17, wherein a concentration of the silver ion or the copper ion in the solution is in a range of 2.5 mmol/L to 30 mmol/L.

* * * * *